United States Patent [19]

Dellaria et al.

[11] Patent Number: 5,432,194
[45] Date of Patent: * Jul. 11, 1995

[54] (4-ALKOXYPYRAN-4-YL) SUBSTITUTED ARYLALKYLARYL-, ARYALKENYLARYL-, AND ARYALKYNYLARYLUREA INHIBITORS OF 5-LIPOXYGENASE

[75] Inventors: Joseph F. Dellaria, Lindenhurst; Anwer Basha, Lake Forest; Lawrence A. Black, Vernon Hills; Linda J. Chernesky, Arlington Heights; Wendy Lee, Chicago, all of Ill.

[73] Assignee: Abbott Laboratories, Abbott Park, Ill.

[ * ] Notice: The portion of the term of this patent subsequent to Sep. 13, 2011 has been disclaimed.

[21] Appl. No.: 236,001

[22] Filed: May 9, 1994

Related U.S. Application Data

[63] Continuation-in-part of Ser. No. 61,988, May 14, 1993, Pat. No. 5,346,914.

[51] Int. Cl.$^6$ .................. A61K 31/35; C07D 309/10
[52] U.S. Cl. ................................. 514/460; 549/419
[58] Field of Search ............ 514/460, 311, 314, 402, 514/227.5, 231.5, 255, 204; 548/311.1, 315.7; 547/419; 544/58.4, 176, 315, 316, 318, 388

[56] References Cited

U.S. PATENT DOCUMENTS

| | | | |
|---|---|---|---|
| 3,671,539 | 6/1972 | Saucy | 549/419 X |
| 4,897,382 | 1/1990 | Della Valle et al. | 514/25 |
| 5,155,229 | 10/1992 | Dipietro et al. | 548/336.1 |
| 5,208,259 | 5/1993 | Bird et al. | 514/460 |
| 5,276,037 | 1/1994 | Dowell et al. | 514/253 |
| 5,346,914 | 9/1994 | Dellapin et al. | 514/402 |

FOREIGN PATENT DOCUMENTS

| | | | |
|---|---|---|---|
| 53-105478 | 9/1978 | Japan | 549/419 |
| 0401664 | 10/1973 | U.S.S.R. | 549/419 |

Primary Examiner—Floyd D. Higel
Attorney, Agent, or Firm—Jerry F. Janssen

[57] ABSTRACT

Compounds of the structure

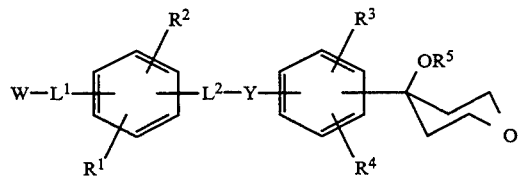

wherein W is selected from

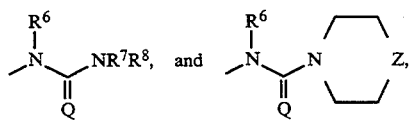

where Q is oxygen or sulfur, $R^6$ and $R^7$ are hydrogen or alkyl, or $R^6$ and $R^7$, together with the nitrogen atoms to which they are attached, define a radical of formula

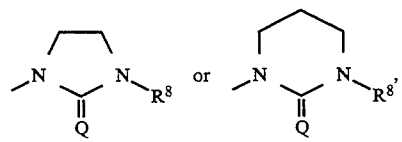

$R^8$ is selected from hydrogen, alkyl, haloalkyl, optionally substituted phenyl, hydroxyalkyl, aminoalkyl, carboxyalkyl, (alkoxycarbonyl)alkyl, and (alkylaminocarbonyl)alkyl; Z is —CH$_2$—, oxygen, sulfur, or —NR$^9$ where $R^9$ is hydrogen or alkyl, L$^1$ and L$^2$ are selected from a valence bond, alkylene, propenylene, and propynylene, $R^1$, $R^2$, $R^3$, and $R^4$ are independently selected from alkyl, haloalkyl, halogen, cyano, amino, alkoxycarbonyl, and dialkylaminocarbonyl, Y is selected from oxygen, —NR$^{10}$, where $R^{10}$ is hydrogen or alkyl, and $$-\underset{\underset{\displaystyle \|}{(O)_n}}{S}-,$$

where n=0, 1, or 2, and $R^5$ is alkyl, inhibit the biosynthesis of leukotrienes. These compounds are useful in the treatment or amelioration of allergic and inflammatroy disease states.

3 Claims, No Drawings

(4-ALKOXYPYRAN-4-YL) SUBSTITUTED ARYLALKYLARYL-, ARYALKENYLARYL-, AND ARYALKYNYLARYLUREA INHIBITORS OF 5-LIPOXYGENASE

CROSS-REFERENCE TO RELATED APPLICATIONS

This application is a continuation-in-part of application Ser. No. 08/061,988 filed May 14, 1993 now U.S. Pat. No. 5,346,914.

TECHNICAL FIELD

This invention relates to compounds having biological activity to inhibit lipoxygenase enzymes, to pharmaceutical compositions comprising these compounds, and to a medical method of treatment. More particularly, this invention concerns certain (4-alkoxypyran-4-yl) substituted arylalkylaryl-, arylalkenylaryl-, and arylalkynylarylurea compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxy-genase action on arachidonate is 5-HPETE which can be reduced to 5-HETE or converted to LTA$_4$. This reactive leukotriene intermediate is enzymatically hydrated to LTB$_4$ or conjugated to the tripeptide glutathione to produce LTC$_4$. LTA$_4$ can also be hydrolyzed nonenzymatically to form two isomers of LTB$_4$. Successive proteolytic cleavage steps convert LTC$_4$ to LTD$_4$ and LTE$_4$. Other products resulting from further oxygenation steps have also been as described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxy-genase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain triether compounds which inhibit lipoxygenase enzyme activity and are useful in the treatment of allergic and inflammatory disease states in which leukotrienes play a role.

The compounds of this invention and the pharmaceutically acceptable salts thereof have the structure

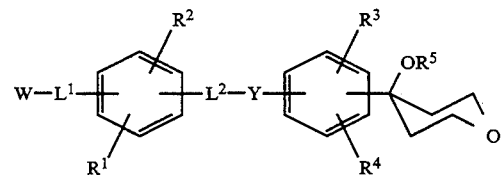

wherein W is selected from the group consisting of

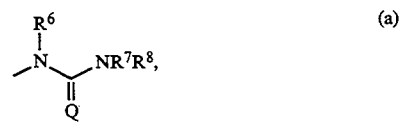 (a)

and

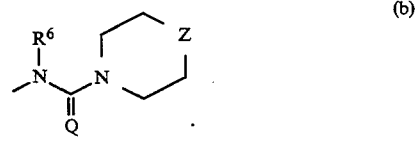 (b)

where Q is oxygen or sulfur, $R^6$ and $R^7$ are independently selected from the group consisting of hydrogen and alkyl of one to four carbon atoms, provided that when $L^1$ is a valence bond, $R^6$ is alkyl of one to four carbon atoms, or $R^6$ and $R^7$, together with the nitrogen atoms to which they are attached, define a radical of formula

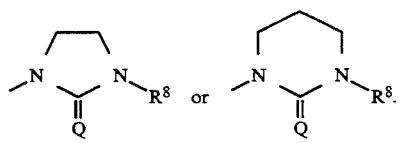

$R^8$ is selected from a) hydrogen; b) alkyl of one to four carbon atoms; c) haloalkyl of one to four carbon atoms; d) phenyl, optionally substituted with alkyl of one to four carbon atoms, alkoxy of one to four carbon atoms, haloalkyl, or halogen; e) hydroxyalkyl of one to four carbon atoms; f) aminoalkyl of one to four carbon atoms; g) carboxyalkyl of one to four carbon atoms; h) (alkoxycarbonyl)alkyl where the alkyl and alkoxy portions each are of one to four carbon atoms; and i) (alkylaminocarbonyl)alkyl, where the alkyl and aminoalkyl portions each are of one to four carbon atoms, and Z is —CH$_2$—, oxygen, sulfur, or —NR$^9$ where R$^9$ is hydrogen or alkyl of one to four carbon atoms.

L$^1$ is a valence bond or is selected from alkylene of one to three carbon atoms, propenylene, and propynylene. R$^1$, R$^2$, R$^3$, and R$^4$ are independently selected from alkyl of one to four carbon atoms, alkoxy of one to four carbon atoms, haloalkyl, halogen, cyano, amino, alkoxycarbonyl of one to four carbon atoms, and dialkylaminocarbonyl where the alkyl portions are each of one to four carbon atoms. L$^2$ is a valence bond or is selected from alkylene of one to three carbon atoms, propenylene, and propynylene, Y is selected from the group consisting of oxygen, >NR$^9$, where R$^9$ is hydrogen or alkyl of one to four carbon atoms, and —S(O)$_n$—, where n=0, 1, or 2, and R$^5$ is alkyl of one to four carbon atoms.

DETAILED DESCRIPTION OF THE INVENTION

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the stucture —NHR' wherein R' is alkyl as previously defined. Example of alkylamino include methylamino, ethylamino, iso-propylamino, and the like.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, iso-propylaminocarbonyl, and the like.

The term "alkanoyl" refers to an alkyl group, as defined above, attached to the parent molecular moiety through a carbonyl group. Alkanoyl groups are exemplified by formyl, acetyl, butanoyl, and the like.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxycarbonyl" represents an ester group; i.e. an alkoxy group attached to the parent molecular moiety through a carbonyl group. Representative alkoxycarbonyl groups include methoxycarbonyl, ethoxycarbonyl, and the like. The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "aminoalkyl" denotes an —NH$_2$ group attached to the parent molecular moiety through an alkylene group. Representative aminoalkyl groups include 2-amino-1-ethylene, 3-amino-1-propylene, 2-amino-1-propylene, and the like.

The term "carboxyalkyl" denotes a —CO$_2$H group attached to the parent molecular moiety through an alkylene group. Representative carboxyalkyl groups include, 1-carboxyethyl, 2-carboxyethyl, 1-carboxypropyl, and the like.

The term "(alkoxycarbonyl)alkyl" denotes an alkoxycarbonyl group, as defined above, attached to the parent molecular moiety through an alkylene group. Representative (alkoxycarbonyl)alkyl groups include ethoxycarbonylmethyl, ethoxycarbonylethyl, methoxycarbonylpropyl, and the like.

The term "(alkylaminocarbonyl)alkyl" denotes an alkylaminocarbonyl group, as defined above, attached to the parent molecular moiety through an alkylene group. Examples of (alkylaminocarbonyl)alkyl groups include methylaminocarbonylmethyl, methylaminocarbonylpropyl, isopropylaminocarbonylmethyl, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

In one preferred embodiment, the compounds of this invention have the structure

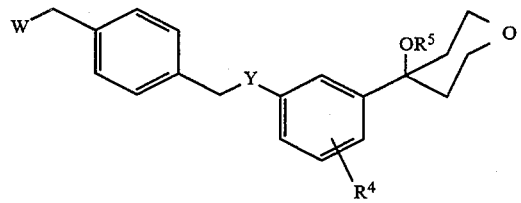

wherein R$^4$ is hydrogen or halogen, and W, Y, and R$^5$ are as defined above.

Examples of compounds of this embodiment include, but are not limited to:

4-{3-[4-((N',N'-dimethylaminocarbonyl)aminomethyl)benzyloxy]-5-fluorophenyl}-4-methoxytetrahydropyran, 4-{3-[4-((N',N'-dimethylaminocarbonyl)aminomethyl)benzyloxy]phenyl}-4-methoxytetrahydropyran, 4-{3-[4-((N',N'-dimethylaminocarbonyl)aminomethyl)benzylthio]-5-fluorophenyl}-4-methoxytetrahydropyran, 4-{3-[4-((N',N'-dimethylaminocarbonyl)aminomethyl)benzylthio]phenyl}-4-methoxytetrahydropyran, 4-{3-[4-((N',N'-dimethylaminocarbonyl)aminomethylbenzyl)amino]phenyl}-4-methoxytetrahydropyran, 4-{3-[4-(((N',N'-dimethylaminocarbonyl)-N-methylamino)methyl)benzyloxy]-5-fluorophenyl}-4-methoxytetrahydropyran, 4-{3-[4-(2-imidazolidinon-1-ylmethyl)benzyloxy]-5-fluorophenyl}-4-methoxytetrahydropyran,
4-{3-[4-(imidazolidin-2-on-1-ylmethyl)benzyloxy]-phenyl}-4-methoxytetrahydropyran,
4-{3-[4-(imidazolidin-2-on-1-ylmethyl)benzylthio]-5-fluorophenyl}-4-methoxytetrahydropyran, and
4-{3-[4-(imidazolidin-2-on-1-ylmethyl)benzylthio]-5-fluorophenyl}-4-methoxytetrahydropyran.

In another preferred embodiment, the compounds of this invention have the structure

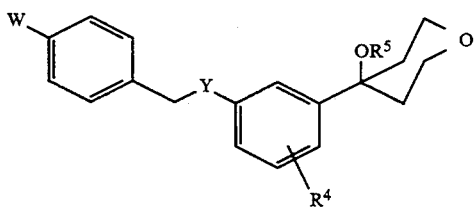

wherein $R^4$ is hydrogen or halogen, and W, Y, and $R^5$ are as defined above.

Examples of compounds of this embodiment include, but are not limited to:

4-{3-[4-((N',N'-dimethylaminocarbonyl)-N-methylamino)benzyloxy]-5-fluorophenyl}-4-methoxytetrahydropyran,
4-{3-[4-((N',N'-dimethylaminothiocarbonyl)-N-methylamino)benzyloxy]-5-fluorophenyl}-4-methoxytetrahydropyran,
4-{3-[4-((N',N'-dimethylaminocarbonyl)-N-methylamino)benzyloxy]phenyl}-4-methoxytetrahydropyran,
4-{3-[4-((N',N'-dimethylaminocarbonyl)-N-methylaminobenzyl)amino]phenyl}-4-methoxytetrahydropyran,
4-{3-[4-((N',N'-dimethylaminothiocarbonyl)-N-methylaminobenzyl)-amino]phenyl}-4-methoxytetrahydropyran,
4-{3-[4-((N',N'-dimethylaminocarbonyl)-N-methylamino)benzylthio]phenyl}-4-methoxytetrahydropyran,
4-{3-[4-((N',N'-dimethylaminocarbonyl)-N-methylamino)benzylthio]-5-fluorophenyl}-4-methoxytetrahydropyran,
4-{3-[4-((aminocarbonyl)amino)benzyloxy]-5-fluorophenyl}-4-methoxytetrahydropyran,
4-{3-[4-((aminocarbonyl)-N-methylamino)benzyloxy]-5-fluorophenyl}-4-methoxytetrahydropyran,
4-{3-[4-((N'-methylaminocarbonyl)-N-methylamino)benzyloxy]-5-fluorophenyl}-4-methoxytetrahydropyran,
4-{3-[4-((N'-methylaminocarbonyl)amino)benzyloxy]-5-fluorophenyl}-4-methoxytetrahydropyran,
4-3-[4-((1-piperidinylcarbonyl)-N-methylamino)benzyloxy]-5-fluorophenyl}-4-methoxytetrahydropyran,
4-{3-[4-((1-piperidinylcarbonyl)amino)benzyloxy]-5-fluorophenyl}-4-methoxytetrahydropyran,
4-{3-[4-((4-morpholinocarbonyl)-N-methylamino)benzyloxy]-5-fluorophenyl}-4-methoxytetrahydropyran,
4-{3-[4-((4-morpholinocarbonyl)amino)benzyloxy]-5-fluorophenyl}-4-methoxytetrahydropyran,
4-{3-[4-((4-thiomorpholinocarbonyl)-N-methylamino)benzyloxy]-5-fluorophenyl}-4-methoxytetrahydropyran,
4-{3-[4-((4-thiomorpholinocarbonyl)amino)benzyloxy]-5-fluorophenyl}-4-methoxytetrahydropyran,
4-{3-[4-((1-piperazinylcarbonyl)-N-methylamino)benzyloxy]-5-fluorophenyl}-4-methoxytetrahydropyran,
4-{3-[4-((1-piperazinylcarbonyl)amino)benzyloxy]-5-fluorophenyl}-4-methoxytetrahydropyran,
4-{3-[4-((1-piperazinylcarbonyl)-N-methylamino)benzyloxy]-5-fluorophenyl}-4-methoxytetrahydropyran,
4-{3-[4-(((N'-(3-bromoprop-1-yl)aminocarbonyl)-N-methylamino)benzyloxy]-5-fluorophenyl}-4-methoxytetrahydropyran,
4-{3-[4-(((N'-(3-aminoprop-1-yl)aminocarbonyl)-N-methylamino)benzyloxy]-5-fluorophenyl}-4-methoxytetrahydropyran,
4-{3-[4-(((N'-(3-hydroxyprop-1-yl)aminocarbonyl)-N-methylamino)benzyloxy]-5-fluorophenyl}-4-methoxytetrahydropyran,
4-{3-[4-(((N'-(3-ethoxycarbonylprop-1-yl)aminocarbonyl)-N-methylamino)benzyloxy]-5-fluorophenyl}-4-methoxytetrahydropyran, and
4-{3-[4-(((N'-(3-carboxyprop-1-yl)aminocarbonyl)-N-methylamino)benzyloxy]-5-fluorophenyl}-4-methoxytetrahydropyran.

In another preferred embodiment, the compounds of this invention have the structure

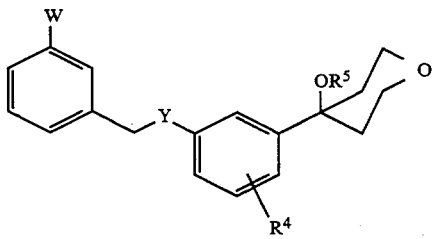

wherein W, Y, $R^4$, and $R^5$ are as defined above.

Examples of compounds of this embodiment include, but are not limited to:

4-{3-[3-((N',N'-dimethylaminocarbonyl)-N-methylamino)benzyloxy]-5-fluorophenyl}-4-methoxytetrahydropyran,
4-{3-[3-((N',N'-dimethylaminocarbonyl)-N-methylamino)benzyloxy]phenyl}-4-methoxytetrahydropyran,
4-{3-[3-((N',N'-dimethylaminocarbonyl)-N-methylaminobenzyl)amino]phenyl}-4-methoxytetrahydropyran,
4-{3-[3-((N',N'-dimethylaminocarbonyl)-N-methylamino)benzylthio]phenyl}-4-methoxytetrahydropyran, and
4-{3-[4-((N',N'-dimethylaminocarbonyl)-N-methylamino)benzylthio]-5-fluorophenyl}-4-methoxytetrahydropyran.

In a particularly preferred embodiment, the compounds of this invention have the structure

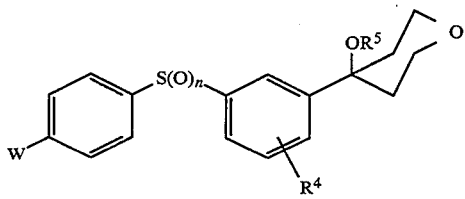

wherein n=0, 1, or 2, $R^4$ is hydrogen or halogen, and W and $R^5$ are as defined above.

Examples of compounds of this embodiment include, but are not limited to:

4-{3-[4-((N', N'-dimethylaminocarbonyl)-N-methylamino)phenylthio]phenyl}-4-methoxytetrahydropyran, 4-{3-[4-((N',N'-dimethylaminocarbonyl)-N-methylamino)-phenylthio]-5-fluorophenyl}-4-methoxytetrahydropyran, 4-{3-[4-((N',N'-dimethylaminocarbonyl)-N-methylamino)phenylsulfinyl]phenyl}-4-methoxytetrahydropyran, 4-{3-[4-((N',N'-dimethylaminocarbonyl)-N-methylamino)phenylsulfonyl]phenyl}-4-methoxytetrahydropyran, 4-{3-[4-((N',N'-dimethylaminocarbonyl)-N-methylamino)-phenylsulfinyl]-5-fluorophenyl}-4-methoxytetrahydropyran, and 4-{3-[4-((N',N'-dimethylaminocarbonyl)-N-methylamino)-phenylsulfonyl]-5-fluorophenyl}-4-methoxytetrahydropyran.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 $\mu M$) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated by data for representative examples presented in Table 1.

TABLE 1

In Vitro Inhibitory Potencies of Compounds of this Invention Against 5-Lipoxygenase from Stimulated $LTB_4$ Formation in Human Whole Blood

| Example | $IC_{50}$ $(10^{-6} M)$ |
| --- | --- |
| 1 | 0.017 |
| 8 | 45% @ 0.025 $\mu M$ |
| 9 | 25% @ 0.10 $\mu M$ |
| 10 | 87% @ ).10 $\mu M$ |
| 11 | 1.8 |
| 17 | 13% @ 200 $\mu M$ |
| 28 | 100% @ 0.78 $\mu M$ |
| 29 | 94% @ 0.10 $\mu M$ |
| 31 | 0.07 |
| 33 | 0.08 |
| 35 | 0.03 |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carder and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of this Invention

The compounds of this invention can be prepared by a variety of synthetic routes. Representative procedures are outlined as follows. It should be understood that $R^5$, $R^6$, $R^7$, $R^8$, and W as used herein correspond to the groups identified above.

A general route to the compounds of this invention is shown in Scheme 1. Reaction of 2, prepared as described in EPA 375 404, with sodium hydride and 1 in DMF provides the desired arylalkylaryl ether 3. Reaction of aniline 4, prepared as described below, or thiophenol 6, prepared as described in EPA 495 594, with sodium hydride and 1 in DMF produces arylalkylaryl amine 5, or arylalkylaryl thioether 7, respectively.

Scheme 1

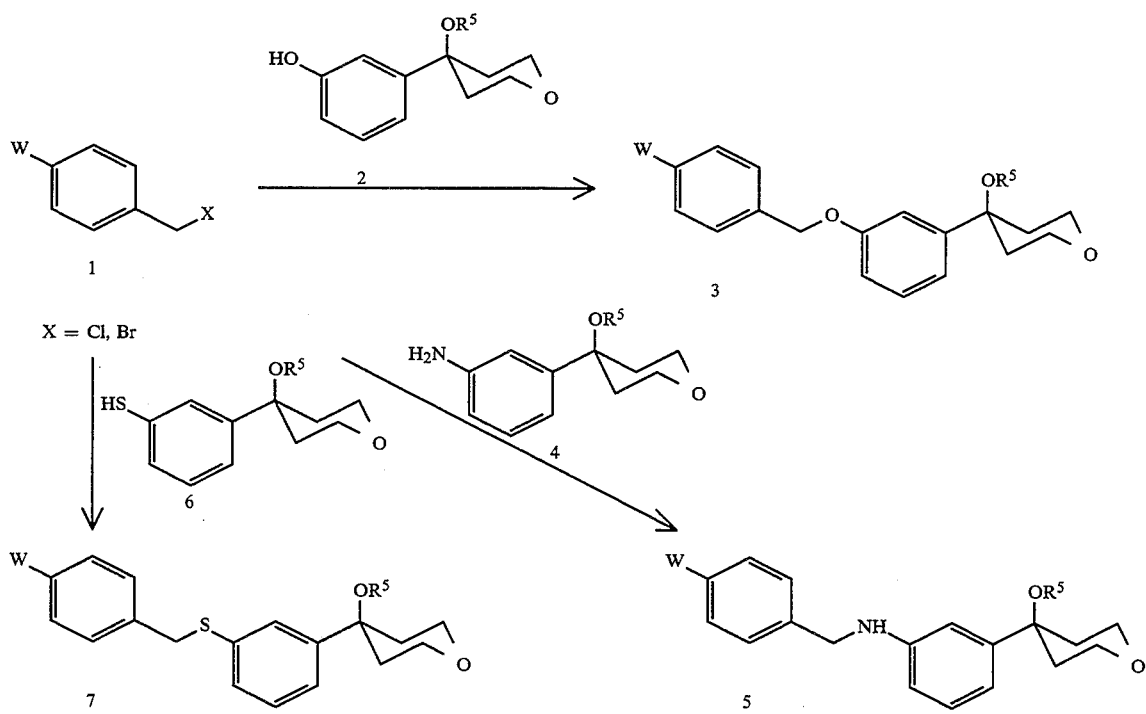

The preparation of compounds where R[6] is alkyl is shown in Scheme 2. 4-aminobenzyl alcohol is reacted with tert-butyldimethylsilyl chloride to form 9, which is then diacylated by treatment sodium acetate and acetic anhydride according to the method of Corley, R. S. and Blout, E. R., *J. Am. Chem. Soc.* 1947, 69, 755, 761 to form 10. Conversion of 10 to the bromide is accomplished as described by Aizupurua, J. M., Cossio, F. P., and Paloma, C., *J. Org. Chem.* 1986, 51, 4941. Arylalkyl-aryl ether 12 is then prepared from bromide 11 as described in scheme 1. Treatment of 12 with one equivalent of LiOH results in removal of one acetyl group to form 13, which is then alkylated by treatment with NaH and the desired alkyl halide to form 14. The second acyl group is removed by treatment of 14 with KOH to form key intermediate 15, which can be reacted with trimethylsilylisocyanate to form 16, or deprotonated with an alkyllithium reagent and acylated with the desired carbamyl chloride to form 17.

Scheme 2

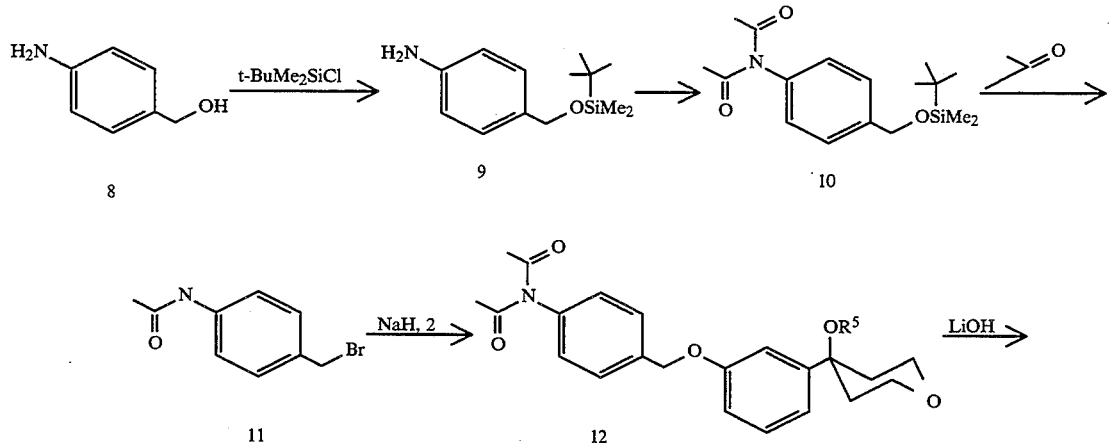

-continued
Scheme 2

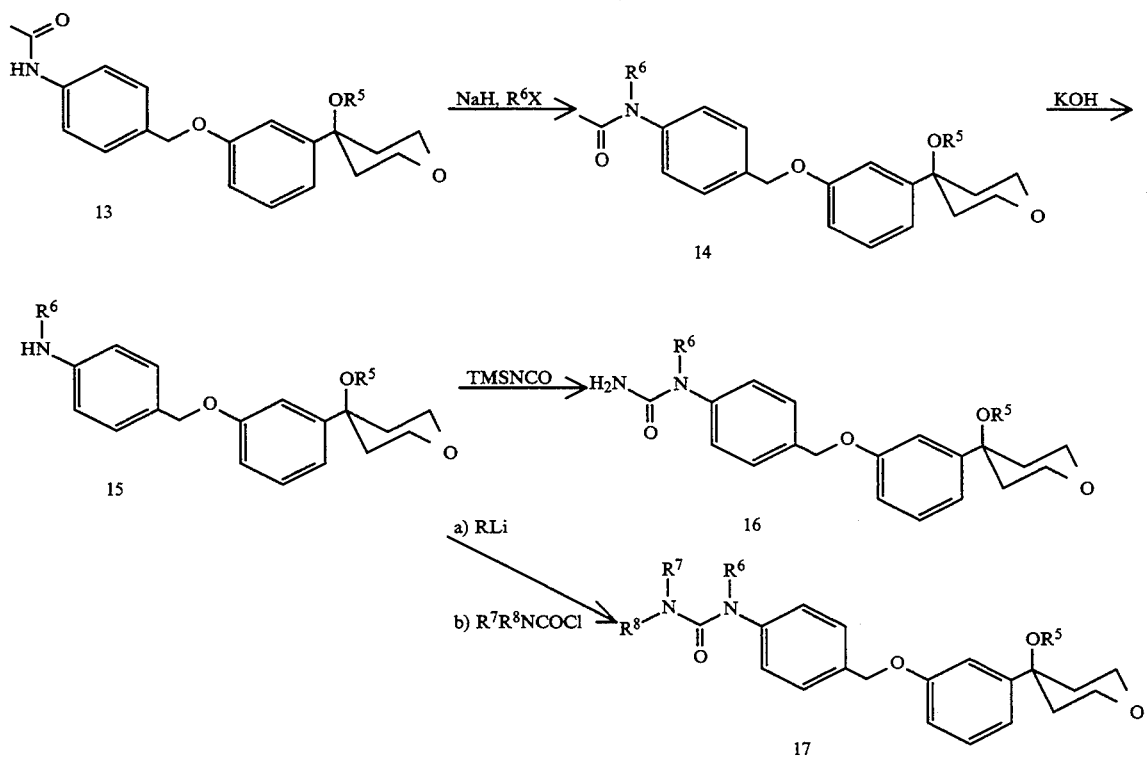

The preparation of compounds where $R^6$ is H is outlined in Scheme 3. Reaction of diacyl compound 12 with KOH produces amine 18 which is then treated with triphosgene to form isocyanate 19. Reaction of 19 with the desired amine produces 20.

Scheme 3

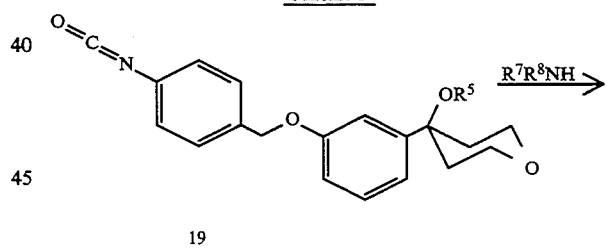

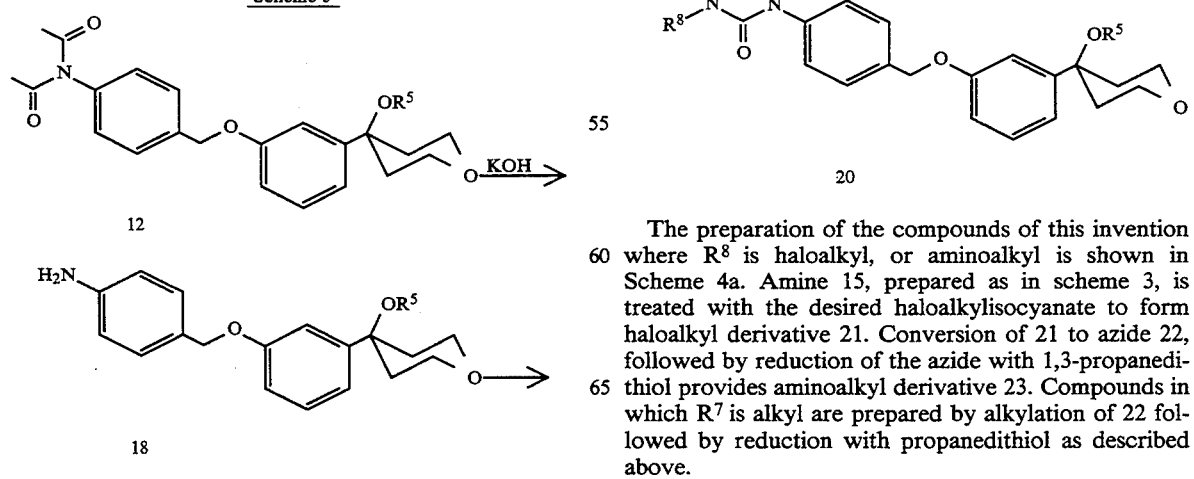

The preparation of the compounds of this invention where $R^8$ is haloalkyl, or aminoalkyl is shown in Scheme 4a. Amine 15, prepared as in scheme 3, is treated with the desired haloalkylisocyanate to form haloalkyl derivative 21. Conversion of 21 to azide 22, followed by reduction of the azide with 1,3-propanedithiol provides aminoalkyl derivative 23. Compounds in which $R^7$ is alkyl are prepared by alkylation of 22 followed by reduction with propanedithiol as described above.

Scheme 4a

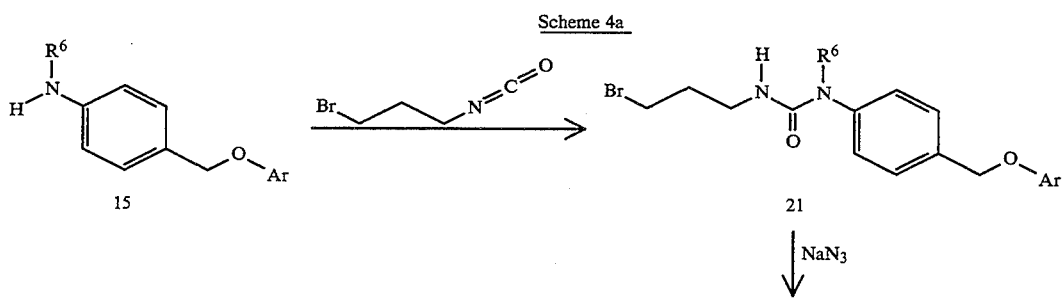

The preparation of the compounds of this invention where $R^8$ is hydroxyalkyl, carboxyalkyl, (alkoxycarbonyl)alkyl, or (alkylaminocarbonyl)alkyl, is shown in or reduced as described above to prepared the derivatives wherein $R^7$ is H. The (alkylaminocarbonyl)alkyl derivatives are prepared from esters 25 and 26, or acids 27 and 29 by standard synthetic methods.

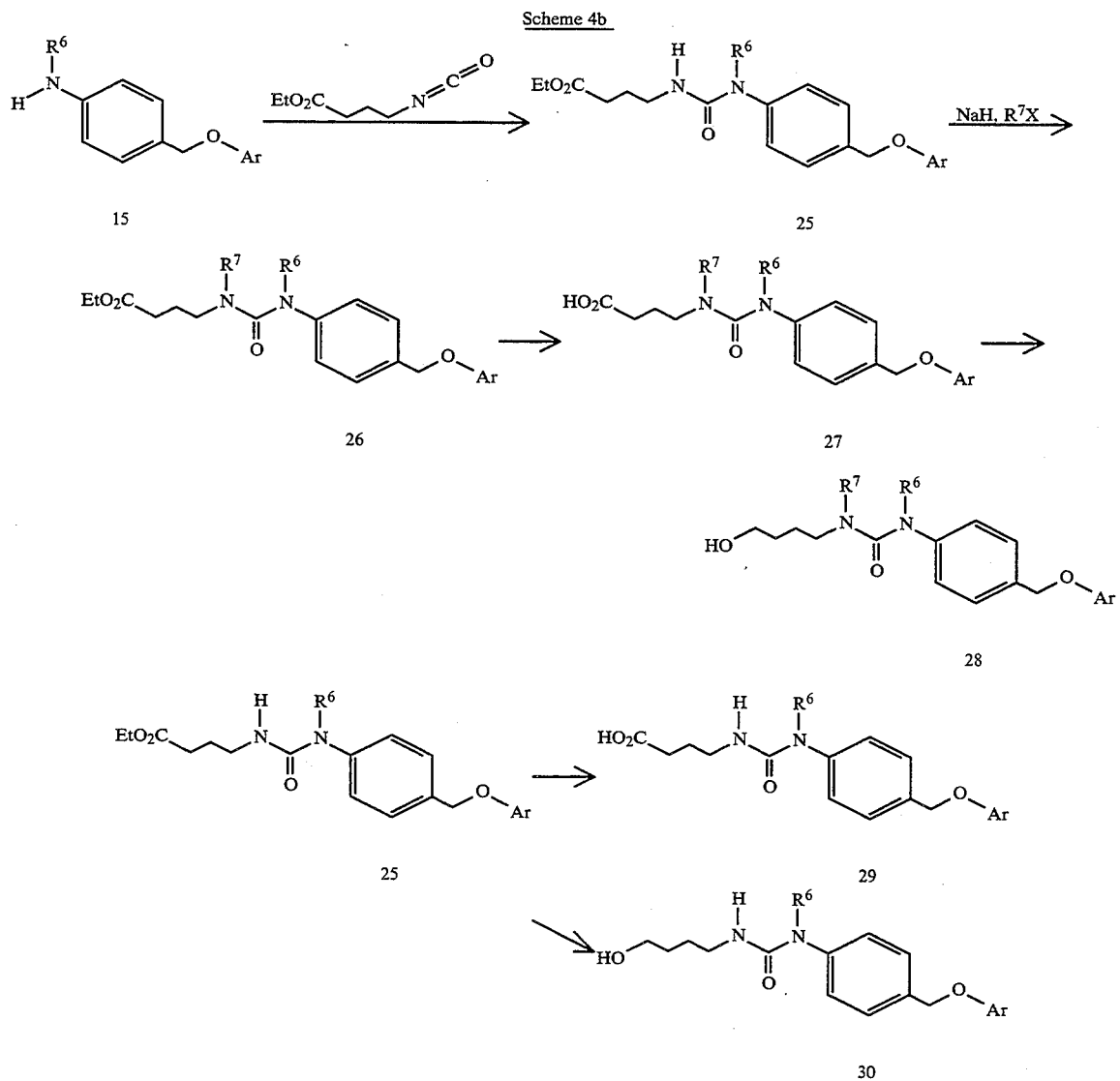

Scheme 4b. Amine 15 is treated with an alkoxycarbonylalkylisocyanate to provide the alkoxycarbonylalkyl derivative 25, which can be alkylated by treatment with NaH and $R^7X$. Hydrolysis of the ester provides (alkoxycarbonyl)alkyl derivative 27, and reduction of 26 with lithium borohydride or 27 with $BH_3$ provides the hydroxyalkyl compound 28. Ester 25 is hydrolyzed The preparation of the arylpropynyl-, arylpropenyl-, and arylpropyl-aryl ethers is shown in Scheme 5. 4-iodoaniline is converted to urea 31 by acylation with dimethylcarbamyl chloride, followed by alkylation with NaH and MeI. Coupling of 31 with propargyl alcohol provides propynol 32 which is converted to chloride 31 by treatment with phosphorus trichloride.

scheme 1. Catalytic hydrogenation of 13 provides saturated compound 35.

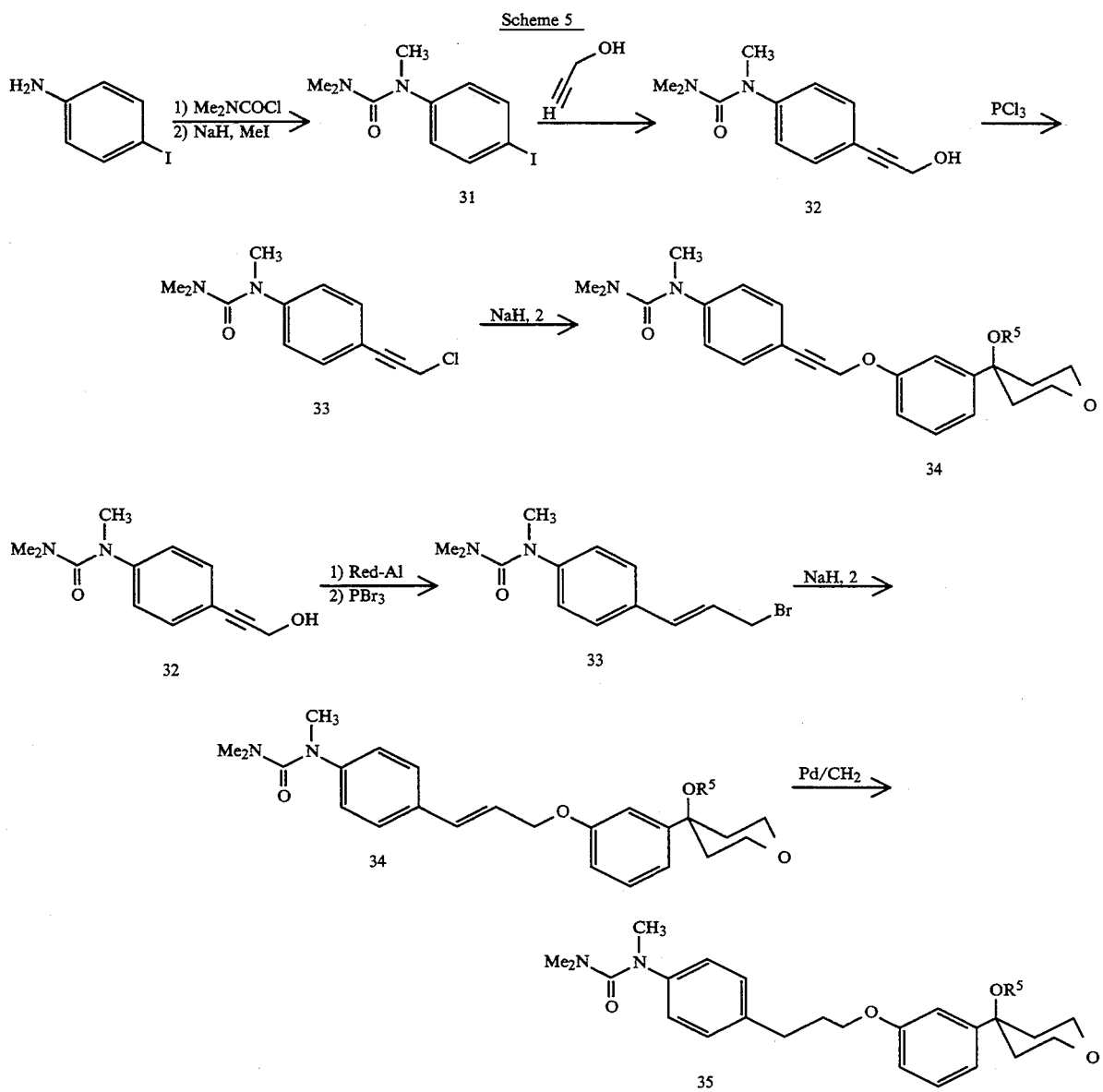

The desired arylpropynyl-aryl ether 34 is prepared as described in scheme 1.

Treatment of alkynol 32 with Red-Al (sodium bis(2-methoxyethoxy)aluminum hydride) and conversion of the resulting allylic alcohol to the bromide with phosphorus tribromide provides 33, which is converted to the desired arylpropenyl-aryl ether 34 as described in In a preferred embodiment, shown in Scheme 6, aminobenzoic acid 36 is treated with methyl isocyanate to form urea 37. Treatment of 37 with excess NaH and iodomethane produces trimethyl urea 38, which is reduced to benzylic alcohol 39 by treatment with lithium triethylborohydride. Conversion to the benzyl halide and displacement with 2 is accomplished as described in Scheme 1.

Scheme 6

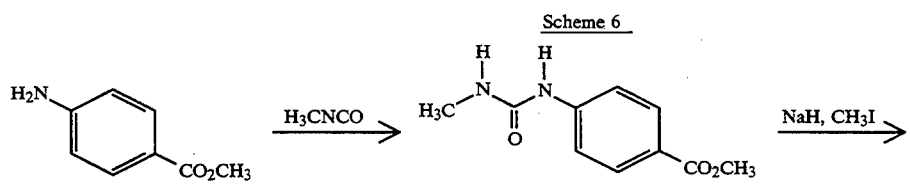

-continued
Scheme 6

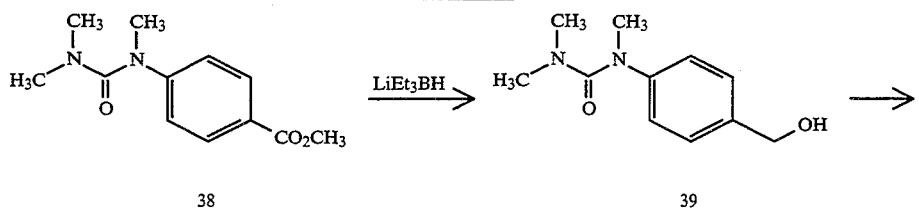

Treatment of p-aminoiodobenzene, 41, with N,N-dimethylcarbamoyl chloride in the presence of triethylamine provides the corresponding p-((N',N'-dimethylaminocarbonyl)amino)iodobenzene, 42. N-methylation is achieved by exposure of the urea to NaH and MeI in a 1:1 THF:DMF solution. Exposure of the trimethylurea and phenylthiol (prepared as described in EP 420511 ) to standard Ulmann coupling conditions provides the title compound, 44.

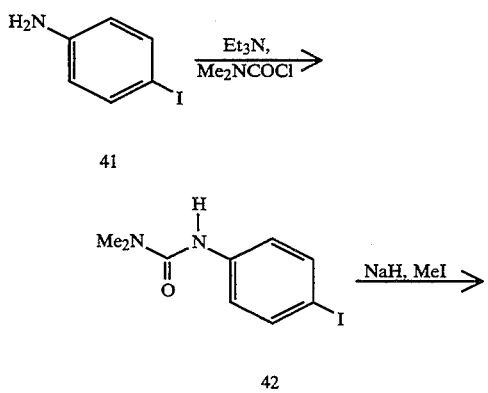

-continued
Scheme 7

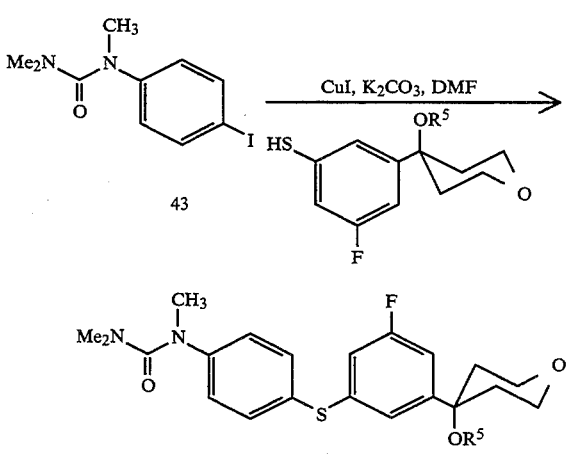

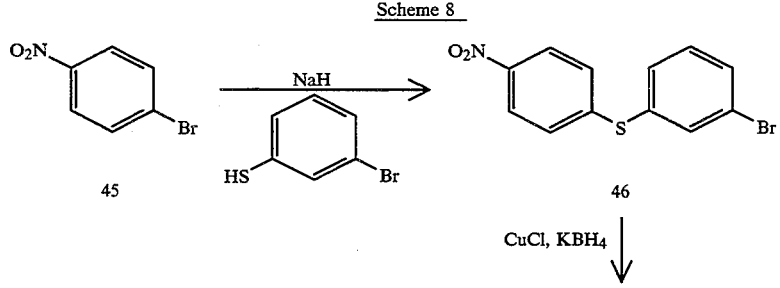

Scheme 8

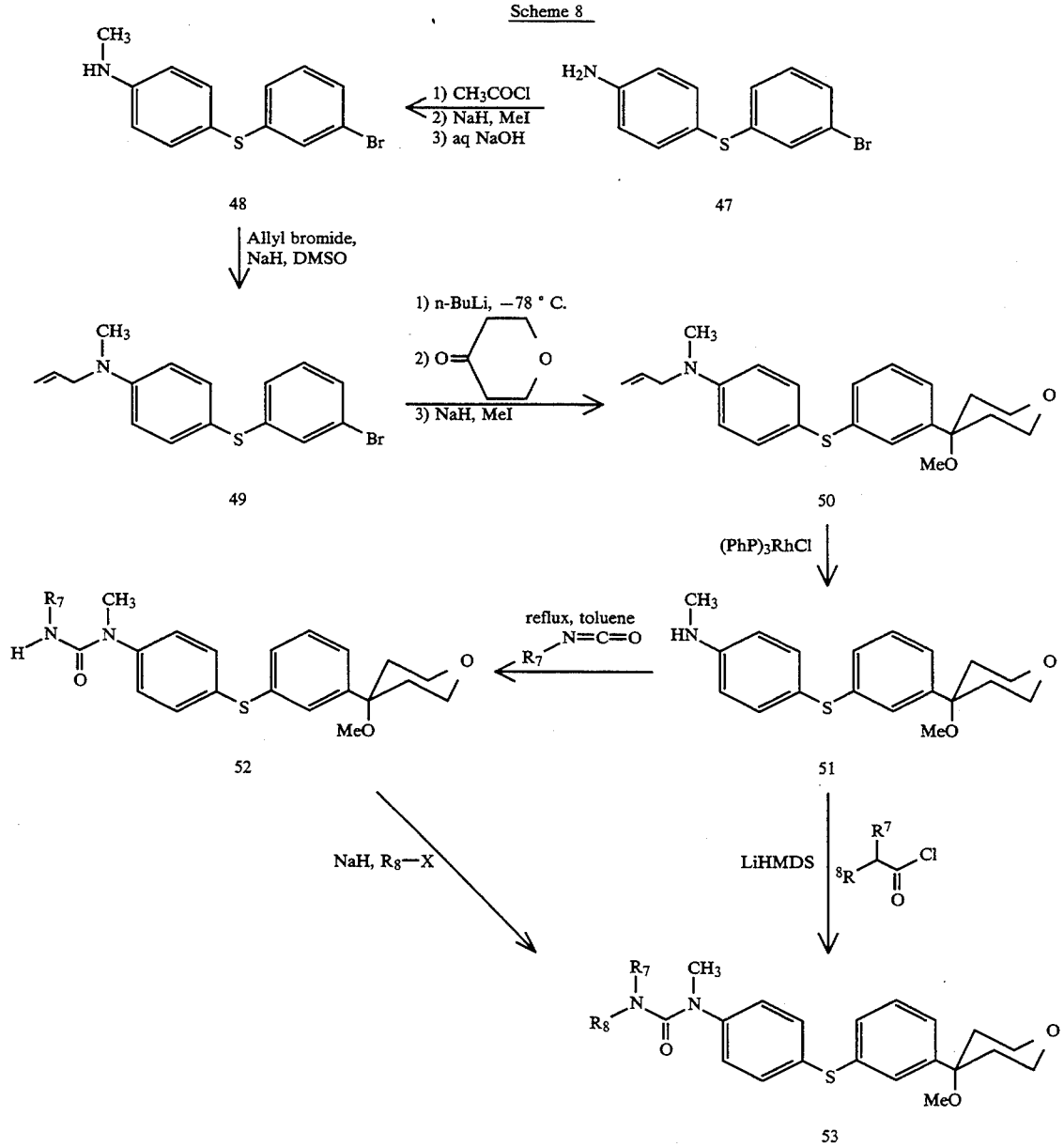

Condensation of the sodium anion of m-bromobenzenthiol with p-nitrobromobenzene, 45, provided the diphenylthioether, 46. Reduction of the nitro-group with the complex borohydride reagent formed by adding KBH$_4$ to CuCl according to the procedure of He, Y.; et. al. (Synth. Commun. 1989, 19, 3047–3050) provided the coresponding aniline, 47. Acetlyation with acetyl chloride and pyridine in dry THF, followed by N-alkylation with NaH and MeI, and subsequent deacylation with aqueous sodium hydroxide provided the N-methyl aniline, 48. Allylation of 48 by reaction of the anion of 48 with allyl bromide in dimethyl sulfoxide provides the N-allyl product 49. Metallation of bromide 49 and condensation with tetrahydropyan-4-one provides tertiary alcohol which is methylated to produce 50. Removal of the N-allyl protecting group is achieved by exposure of 50 to tristriphenyl phosphine rhodium (I) chloride to produce 51. Deprotonation of the N-methyl aniline with lithium hexamethylsilazide and treatment of the anion with the desried N,N-dialkylcarbamoyl chloride provides the trialkylurea analog 53. Sequential treatment of the N-methyl aniline, 51, with the desired N-alkylisocyanate in refluxing toluene provides 52. Subsequent alkylation of the terminal nitrogen by treatment with NaH and the desired alkyl halide also provides the desired trialkylureas, 53.

The foregoing may be better understood from the following Examples, which are presented for the purpose of illustration and not intended to limit the scope of the inventive concept.

EXAMPLE 1

Preparation of 4-{3-[4-((N′,N′-dimethylaminocarbonyl)-N-methylamino)benzyloxy]-5-fluorophenyl}-4-methoxytetrahydropyran Step 1. Preparation of methyl 4-(N-methylaminocarbonyl)aminobenzoate.

A solution of methyl 4-aminobenzoate (15 g, 99 mmol), and methyl isocyanate (11.8 mL, 200 mmol) in toluene (400 mL) was heated at 100° C. under $N_2$ for 3 hours during which time a precipitate formed slowly. Additional methyl isocyanate (11.8 mL, 200 mmol) was added and heating was continued for 2 hours. The reaction mixture was cooled to 0° C. and filtered. The precipitate was washed with ether and vacuum-dried to give methyl 4-(N-methylaminocarbonyl)aminobenzoate as a colorless solid (17.5 g, 85%).

Step 2. Preparation of methyl 4-[(N',N'-dimethylaminocarbonyl)-N-methylamino]benzoate.

To a 0° C. suspension of NaH (80% oil dispersion, 3.60 g, 120 mmol) in THF (200 mL) under $N_2$ was added a solution of methyl 4-(N-methylaminocarbonyl)aminobenzoate (10.0 g, 48 mmol), prepared as in step 1, in THF (40 mL). The reaction mixture was stirred at 0° C. until gas evolution ceased, then the cold bath was removed and stirring was continued for 1.5 hours. A solution of iodomethane (6.6 mL, 106 mmol) in DMF (24 mL) was added and the reaction mixture was stirred for 72 hours at ambient temperature. NaH (2.0 g), and iodomethane (5.0 mL) were then added and the reaction mixture was stirred for an additional 2 hours. The reaction mixture was poured slowly into ice-water and the organics were stripped off in vacuo. The aqueous solution was extracted with ethyl acetate (10 x). The combined organic layers were dried over $MgSO_4$, filtered, and concentrated. Pure methyl 4-[(N', N'-dimethylaminocarbonyl)-N-methylamino]benzoate (6.62 g, 58%) was obtained as a colorless oil which crystallized on standing after chromatography on silica gel (40%, then 50% ethyl acetate/hexanes). mp 71°-73° C.

Step 3. Preparation of 4-[(N', N'-dimethylaminocarbonyl)-N-methylamino]benzyl alcohol.

To a 0° C. solution of methyl 4-[(N', N'-dimethylaminocarbonyl)-N-methylamino]benzoate (1.50 g, 6.35 mmol), prepared as in step 2, in THF (11.4 mL) was added lithium triethylborohydride (1.0M solution in THF, 14 mmol). The reaction mixture was stirred for 1 hour. Water (3.0 mL) and $H_2O_2$ (30% aqueous solution, 5.0 mL) were added and the reaction mixture was stirred at 45° C. for 20 min. Aqueous HCL (6M, 8.0 mL) was added and the reaction mixture was stirred at reflux for 14 hours. The reaction mixture was cooled to ambient temperature and poured into ethyl acetate. The aqueous phase was extracted three times with ethyl acetate. The combined organic layers were dried over $MgSO_4$, filtered, and concentrated in vacuo. 4-[(N', N'-dimethylaminocarbonyl)-N-methylamino]benzyl alcohol (797 mg, 61%) was isolated as a colorless solid by chromatography on silica gel (ethyl acetate). mp 65°-66° C.

Step 4. Preparation of 4-[(N',N'-dimethylaminocarbonyl)-N-methylamino]benzyl chloride.

To a stirred solution at −23° C. under $N_2$ of 4-[(N',N'-dimethylaminocarbonyl)-N-methylamino]benzyl alcohol (77.0 mg, 0.37 mmol), prepared as in step 4, in dry $CH_2Cl_2$ (3.7 mL) was added triethylamine (67.0 μL, 0.48 mmol), and methanesulfonyl chloride (34.0 μL, 0.44 mmol). The reaction mixture was stirred at ambient temperature until TLC indicated complete reaction (∼5 hours). The resultant solution was poured into ethyl acetate and the organic phase was washed (2 X, water; 2 X, brine), dried ($MgSO_4$), filtered and concentrated in vacuo. Purification by flash chromatography on silica gel (70% ethyl acetate/hexane) provided 4-[(N',N'-dimethylaminocarbonyl)-N-methylamino]-benzyl chloride (56.0 mg, 67.0%) as a colorless oil which crystallized on standing at −25° C. mp 38.5°-39° C. $^1H$ NMR (300 MHz, $CDCl_3$) δ7.34 (2H, d, J=8.5 Hz), 7.04 (2H, d, J=8.5 Hz), 4.57 (2H, s), 3.22 (3H, s), 2.71 (6H, s). MS m/e 227 (M+H)+, 244 (M+$NH_4$)+.

Step 5. Preparation of 4-{3-[4-((N',N'-dimethylaminocarbonyl)-N-methylamino)benzyloxy]-5-fluorophenyl}-4-methoxytetrahydropyran.

4-methoxy-4-(5-fluoro-phenoxy-3-yl)tetrahydropyran (58.0 mg, 0.26 mmol), prepared as described in EPA 375-404, was dissolved in dry DMF and sodium hydride (16.0 mg, 0.39 mmol) was added to the mixture. After gas evolution ceased, a solution of 4-[(N',N'-dimethylaminocarbonyl)-N-methylamino]benzyl chloride, (53.0 mg, 0.23 mmol) prepared as in step 4, in dry DMF (1.0 mL) was added. The reaction was stirred for 1 hour at ambient temperature and quenched by adding excess saturated aqueous ammonium chloride. The resulting biphasic mixture was poured into ethyl acetate and the organic phase was washed (1 X, saturated aqueous ammonium chloride; 2 X, brine), dried ($MgSO_4$), filtered and concentrated in vacuo to give an oil. Purification by flash chromatography on silica gel (50% ethyl acetate/hexane) provided 4-{3-[4-((N',N'-dimethylaminocarbonyl)-N-methylamino)-benzyloxy]-5-fluorophenyl}-4-methoxytetrahydropyran as a colorless oil (34.0 mg, 35.0%). $^1H$ NMR (300 MHz, $CDCl_3$) δ7.39 (2H, d, J=8.5 Hz), 7.08 (2H, d, J=8.5 Hz), 6.80 (1H, br s), 6.72 (1H, br dt, J=9.9, 1.9, 1.9 Hz), 6.63 (1H, dt, J=9.9, 2.0, 2.0 Hz), 5.0 (2H, s), 3.87 to 3.68 (4H, m), 3.22 (3H, s), 2.98 (3H, s), 2.72 (6H, s), 2.03 to 1.85 (4H, m). MS m/e 417 (M+H)+, 434 (M+$NH_4$)+. Analysis calc'd for $C_{23}H_{29}FN_2O_4$: C, 66.33; H, 7.02; N, 6.73. Found: C, 66.27; H, 6,84; N, 6.71.

EXAMPLE 2

Preparation of 4-{3-[4-((N',N'-dimethylaminothiocarbonyl)-N-methylamino)benzyloxy]-5-fluorophenyl}-4-methoxytetrahydropyran The desired compound is prepared by treatment of 4-{3-[4-((N',N'-dimethylaminocarbonyl)-N-methylamino)benzyloxy]-5-fluorophenyl}-4-methoxytetrahydropyran, prepared as in Example 1 with Lawesson's Reagent ([2,4-bis(4-methoxyphenyl)-1,3-dithia-2,4-diphosphetane-2,4-disulfide) according to the method of Katah, A., Kashima, C., and Omote, Y. *Heterocycles,* 1982, 19(12), 2283.

EXAMPLE 3

Preparation of 4-{3-[4-((N',N'-dimethylaminocarbonyl)-N-methylamino)benzyloxy]phenyl}-4-methoxytetrahydropyran The desired compound is prepared according to the method of Example 1, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 4

Preparation of 4-{3-[4-((N',N'-dimethylaminocarbonyl)-N-methylaminobenzyl)amino]phenyl}-4-methoxytetrahydropyran Step 1. Preparation of N-t-Boc-3-bromoaniline.

3-bromoaniline (10 g, 58.1 mmol) and di-tert-butyldicarbonate (19.0 g, 87.1 mmol) were dissolved in 2M aqueous sodium hydroxide and heated at reflux for 1 hour. After cooling to ambient temperature, the reaction mixture was extracted with ethyl acetate. The organic layer was washed (saturated aqueous ammonium chloride, 1×; water, 1×; and brine, 2×), dried (MgSO$_4$), filtered, concentrated in vacuo, and dried under high vacuum to provide N-t-Boc-3 bromoaniline as a colorless solid (15.8 g, 100%). mp 83° C. $^1$H NMR (300 MHz, CDCl$_3$) δ7.66 (1H, br m), 7.08–7.23 (3H, m), 6.46 (1H, br s), 1.52 (9H, s). MS m/e 272/274 (M+H)$^+$, 289/291 (M+NH$_4$)$^+$.

Step 2. Preparation of 4-(3-t-butyloxycarbonylaminophenyl)-4-hydroxytetrahydropyran.

A flask charged with N-t-Boc-3 bromoaniline (6.0 g, 22.0 mmol), prepared as in step 1, THF (88 mL), and a magnetic stirbar was cooled to −78° C. under a flow of nitrogen. To this solution was added n-butyllithium (22 mL of 2.5M solution in hexanes, 55.1 mmol) in a dropwise fashion from a syringe. The resulting solution was stirred at −78° C. for 1.5 hours. Tetrahydro-4H-pyran-4-one (2.5 mL, 26.5 mmol) was added neat to the solution, the cooling bath was removed, and the resulting solution was stirred at ambient temperature for 0.5 hours. The reaction was quenched carefully by adding excess saturated aqueous ammonium chloride. The mixture was partitioned between ethyl acetate and saturated aqueous ammonium chloride. The organic layer was washed (1×, saturated aqueous ammonium chloride; 2×, water; 1×, brine), dried (MgSO$_4$), and concentrated in vacuo to provide a solid. Recrystallization from chloroform/hexanes provided 4-(3-t-butyloxycarbonylaminophenyl)-4-hydroxytetrahydropyran as a beige solid (4.31 g, 67%). mp 140°–142° C. $^1$H NMR (300 MHz, CDCl$_3$) δ7.55 (1H, br m), 7.21–7.32 (2H, m), 7.14 (1H, dt, J=7, 1, 1 Hz), 6.52 (1H, br s), 3.93 (2H, td, J=12, 12, 2.5 Hz), 3.87 (2H, ddd, J=12, 6, 2 Hz), 2.19 (2H, ddd, J=13.5, 12.5, 6 Hz), 1.69 (2H, br t, J=13.5 Hz), 1.52 (9H, s); MS m/e 293 (M+NH$_4$—H$_2$O)$^+$, 311 (M+NH$_4$)$^+$.

Step 3. Preparation of 4-(3-aminophenyl)-4-hydroxytetrahydropyran.

To an ice-cooled solution of 4-(3-t-butyloxycarbonylaminophenyl)-4-hydroxytetrahydropyran (2.0 g, 6.8 mmol), prepared as in step 2, in dichloromethane (14 mL) was added trifluoroacetic acid (14, mL). The resulting solution was stirred for 0.25 hours at 0° C. and 1 hour at ambient temperature. The volatiles were removed in vacuo and the resulting solution was basified with saturated aqueous potassium carbonate. The resulting mixture was diluted with dichloromethane and the layers separated. The aqueous layer was extracted (4×, dichloromethane). The combined organic layers were dried (MgSO$_4$), and concentrated in vacuo to provide a solid. Trituration with hexanes provided 4-(3-aminophenyl)-4-hydroxytetrahydropyran as a colorless solid (1.01 g, 77%). mp 154°–155° C. $^1$H NMR (300 MHz, CDCl$_3$) δ7.17 (1H, dt, J=7.5, 1 Hz), 6.84–6.88 (2H, m), 6.62 (1H, br d, J=7.5 Hz), 3.93 (2H, td, J=12, 12, 2.5 Hz), 3.84 (2H, ddd, J=12, 5, 1.5 Hz), 2.05–32 (4H, m). MS m/e 193 (M+NH$_4$—H$_2$O)$^+$, 211 (M+NH$_4$)$^+$.

Step 4. Preparation of 4-(3-aminophenyl)-4-methoxytetrahydropyran.

To a solution of 4-(3-aminophenyl)-4-hydroxytetrahydropyran (630 mg, 3.26 mmol), prepared as in step 3, in dry DMF (13 mL) was added sodium hydride (326 mg of a 60% oil dispersion). The reaction was stirred at ambient temperature for 1 hour and then methyl iodide (0.24 mL, 3.19 mmol) was added neat. The resulting solution was stirred at ambient temperature for 0.5 hour and quenched with saturated aqueous ammonium chloride. The biphasic solution was extracted with ethyl acetate. The organic layer was washed (1×, saturated aqueous ammonium chloride; 2×, brine), dried (MgSO$_4$), and concentrated in vacuo to provide an oil. Chromatography on silica gel with 20% ethyl acetate/hexanes as the eluant provided 4-(3-aminophenyl)-4-methoxytetrahydropyran as a beige solid (510 mg, 76%). mp 99.0°–100.5° C. $^1$H NMR (300 MHz, CDCl$_3$) δ7.17 (1H, t, J=9 Hz), 6.73–6.82 (2H, m), 6.62 (1H, ddd, J=9, 2, 1 Hz), 3.85 (2H, td, J=10.5, 10.5, 2.5 Hz), 3.81 (2H, ddd, J=10.5, 9, 3 Hz), 2.99 (3H, s), 1.87–2.07 (4H, m). MS m/e 207 (M)$^+$, 225 (M+NH$_4$)$^+$.

Step 5. Preparation of 4-{3-[4-((N',N'-dimethylaminocarbonyl)-N-methylaminobenzyl)-amino]phenyl}-4-methoxytetrahydropyran.

The desired compound is prepared according to the method of Example 1, step 5, except substituting 4-(3-aminophenyl)-4-methoxytetrahydropyran, prepared as in step 4, for 4-methoxy-4-(5-fluoro-phenoxy-3-yl)tetrahydropyran.

EXAMPLE 5

Preparation of 4-{3-[4-((N',N'-dimethylaminothiocarbonyl)-N-methylaminobenzyl)-amino]phenyl}-4-methoxytetrahydropyran The desired compound is prepared according to the method of Example 94608, except substituting N,N-dimethylthiocarbamoyl chloride (38 mg, 0.31 mmol, 1.5 eqiuv) for morpholinocarbamoyl chloride. Chromatography over silica gel (20% ethyl acetae:hexanes) provided the pure title compound as a yellow oil (68 mg, 79%). $^1$H NMR (300 MHz, CDCl$_3$) δ7.18–7.37 (6H; m), 6.97 (2H;dt; J=9 Hz), 3.79–3.89 (4H; m), 3.52 (3H; s), 3.03 (6H; s), 2.97 (3H; s), 1.86–2.06 (4H; m). MS m/e 401 (M+H)$^+$; Analysis calc'd for C$_{22}$H$_{28}$N$_2$O$_2$S$_2$(0.5 H$_2$O): C, 62.09; H, 6.87; N, 6.72. Found: C, 62.23; H, 7.17; N, 6.89.

EXAMPLE 6

Preparation of 4-{3-[4-((N',N'-dimethylaminocarbonyl)-N-methylamino)benzylthio]phenyl}-4-methoxytetrahydropyran The desired compound is prepared according to the method of Example 1, except substituting 4-(3-thiophenyl)-4-methoxytetrahydrofuran, prepared as described in EPA 495 594, for 4-(5-fluoro-3-hydroxyphenyl)-4-methoxytetrahydropyran.

EXAMPLE 7

Preparation of 4-{3-[4-((N',N'-dimethylaminocarbonyl)-N-methylamino)benzylthio]-5-fluorophenyl}-4-methoxytetrahydropyran The desired compound is prepared according to the method of Example 1, except substituting 4-(5-fluoro-3-thiophenyl)-4-methoxytetrahydrofuran, prepared as described in EPA 495 594, for 4-(5-fluoro-3-hydroxyphenyl)-4-methoxytetrahydropyran.

EXAMPLE 8

Preparation of 4-{3-[4-((N',N'-dimethylaminocarbonyl)-N-methylamino)phenylthio]phenyl}-4-methoxytetrahydropyran Step 1. Preparation of N-t-Boc-4-iodoaniline.

The desired compound was prepared according to the method of Example 4, step 1, except substituting 4-iodoaniline for 3-bromoaniline. mp 140°–141° C. $^1$H NMR (300 MHz, CDCl$_3$) δ7.57 (2H, d, J=9 Hz), 7.13 (2H, d, J=9 Hz), 6.43 (1H, br s), 1.52 (1H, br s). MS m/e 320 (M+H)$^+$, 337 (M+NH$_4$)$^+$.

Step 2. Preparation of 3-(4-aminophenylthio)bromobenzene.

A mixture of 3-bromothiophenol (3.00 g, 15.9 mmol), N-t-Boc-4-iodoaniline (5.00 g, 15.9 mmol), prepared as in step 1, CuI (756 mg, 4.00 mmol), and K$_2$CO$_3$ (4.40 g, 31.7 mmol) in DMF was heated at reflux under N$_2$ for 2 hours. The reaction mixture was poured into H$_2$O/ethyl acetate and filtered through a pad of celite. The organic phase was washed twice with saturated aqueous NH$_4$Cl, once with H$_2$O, and twice with brine, dried over MgSO$_4$, filtered, and concentrated in vacuo. Chromatography on silica gel (20% ethyl acetate/hexanes) provided 3-(4-aminophenylthio)bromobenzene (1.56 g, 35%). $^1$H NMR (300 MHz, CDCl$_3$) δ7.32 (2H, dt, J=9, 2, 2 Hz), 7.18–7.24 (2H, m), 6.97–7.07 (2H, m), 6.69 (2H, dt, J=9, 2, 2 Hz), 3.85 (2H, br s). MS m/e 280/282 (M+H)$^+$, 297/299 (M+NH$_4$)$^+$.

Step 3. Preparation of 3-[4-((N',N'-dimethylaminocarbonyl)amino)phenylthio]bromobenzene.

To a solution of 3-(4-aminophenylthio)bromobenzene (415 mg, 1.48 mmol) in CH$_2$Cl$_2$ (7.4 mL) was added triethylamine (0.31 mL, 2.22 mmol) and dimethylcarbamyl chloride (0.34 mL, 3.70 mmol). The reaction mixture was stirred for one hour at ambient temperature and then at reflux for 18 hours, at which time additional triethylamine (3.0 mL), and dimethylcarbamyl chloride (3.0 mL) were added. The reaction mixture was heated at reflux for one hour, then cooled to ambient temperature and poured into ethyl acetate. The solution was washed twice with H$_2$O, twice with brine, dried over MgSO$_4$, filtered, and concentrated in vacuo. Chromatography on silica gel (40% ethyl acetate/hexanes) provided 3-[4-((N', N'-dimethylaminocarbonyl)amino)phenylthio]bromobenzene (362 mg, 70%) as a colorless oil. $^1$H NMR (300 MHz, CDCl$_3$) δ7.37–7.45 (4H, m), 7.23–7.28 (2H, m), 7.06–7.10 (2H, m), 6.38 (1H, br s), 3.07 (6H, s). MS m/e 353/353 (M+H)$^+$, 368/370 (M+NH$_4$)$^+$.

Step 4, Preparation of 3-[4-((N', N'-dimethylaminocarbonyl)-N-methylamino)phenylthio]bromobenzene.

To a solution of 3-[4-((N', N'-dimethylaminocarbonyl)amino)phenylthio]bromobenzene (100 mg, 0.285 mmol), prepared as in step 3, in DMF (2.8 mL) was added NaH (60% oil dispersion, 30.0 mg, 0.745 mmol). The reaction mixture was stirred at ambient temperature for one hour. Iodomethane (22.3 μL, 0.358 mmol) was added and the reaction mixture was stirred at ambient temperature for 17 hours. The reaction mixture was quenched with saturated aqueous NH$_4$Cl and poured into ethyl acetate. The organic phase was washed once with saturated aqueous NH$_4$Cl, once with H$_2$O, and twice with brine, dried over MgSO$_4$, filtered, and concentrated in vacuo. 3-[4-((N', N'-dimethylaminocarbonyl)-N-methylamino)phenylthio]bromobenzene (89.2 mg, 86%) was obtained by chromatography on silica gel (40% ethyl acetate/hexanes). $^1$H NMR (300 MHz, CDCl$_3$) δ7.38 (2H, dt, J=9, 2, 2 Hz), 7.29–7.33 (2H, m), 7.13–7.16 (2H, m), 7.03 (2H, dt, J=9, 2, 2 Hz), 3.24 (3H, s), 2.75 (6H, s). MS m/e 365/367 (M+H)$^+$, 382/384 (M+NH$_4$)$^+$.

Step 5. Preparation of 4-{3-[4-((N',N'-dimethylaminocarbonyl)-N-methylamino)phenylthio]phenyl}-4-hydroxytetrahydropyran.

The desired compound was prepared according to the method of Example 4, step 2, except substituting 3-[4-((N', N'-dimethylaminocarbonyl)-N-methylamino)phenylthio]bromobenzene, prepared as in step 4 for N-t-Boc-3 bromoaniline, and substituting t-butyllithium for n-butyllithium. $^1$H NMR (300 MHz, CDCl$_3$) δ7.46 (1H, m), 7.27–7.38 (4H, m), 7.17 (1H, dt, J=9, 2, 2 Hz), 7.01 (2H, dt, J=9, 2, 2 Hz), 3.82–3.95 (4H, m), 3.22 (3H, s), 2.73 (6H, s), 2.07–2.18 (2H, m), 1.58–1.73 (2H, m). MS m/e 386 (M−H$_2$O+NH$_4$)$^+$, 404 (M+NH$_4$)$^+$.

Step 6. Preparation of 4-{3-[4-((N',N'-dimethylaminocarbonyl)-N-methylamino)phenylthio]phenyl}-4-methoxytetrahydropyran.

The desired compound was prepared according to the method of Example 4, step 4, except substituting 4-{3-[4-((N',N'-dimethylaminocarbonyl)-N-methylamino)-phenylthio]phenyl}-4-hydroxytetrahydropyran for 4-(3-aminophenyl)-4-hydroxytetrahydropyran. $^1$H NMR (300 MHz, CDCl$_3$) δ7.30–7.36 (4H, m), 7.22–7.28 (1H, m), 7.18 (1H, dt, J=9,2,2 Hz), 7.01 (2H, dt, J=9,2,2 Hz), 3.77–3.89 (4H, m), 3.22 (3H, s), 2.96 (3H, s), 2.73 (6H, s), 1.86–2.04 (4H, m). MS m/e 401 (M+H)$^+$, 418 (M+NH$_4$)$^+$; Analysis calc'd for C$_{22}$H$_{28}$N$_2$O$_3$S: C, 65.97; H, 7.05; N, 6.99. Found: C, 65.83; H, 7.02; N, 6.78.

EXAMPLE 9

Preparation of 4-{3-[4-((N',N'-dimethylaminocarbonyl)-N-methylamino)phenylsulfinyl]phenyl}-4-methoxytetrahydropyran The desired compound was prepared by treatment of 4-{3-[4-((N',N'-dimethylaminocarbonyl)-N-methylamino)phenylthio]phenyl}-4-methoxytetrahydropyran, prepared as in Example 8, with m-chloroperbenzoic acid (234 mg, 1.36 mmol) in methylene chloride (9.2 mL) at ambient temperature for 1 h. The reaction was filtered and the filter cake was washed with methylene chloride. The combined filtrates were partitioned between ethyl acetate and water. The organic layer was washed (2×, water; 2×, brine), dried (MgSO$_4$), filtered, and concentrated under vacuum. The residue was chromatographed over silica gel (100% ethyl acetate). The product was recrystallized from ethyl acetate:hexanes to provide the title compound as a colorless solid (273 mg, 71%). mp=104°–106° C.: $^1$H NMR (300 MHz, CDCl$_3$) δ7.68 (1H; q; J=1.5 Hz), 7.58 (2H; d; J=9.5 Hz), 7.47–7.56 (3H, m), 7.07 (2H, d, J=9.5 Hz), 3.78–3.90 (4H, m), 3.22 (3H, s), 2.93 (3H, s), 2.73 (6H, s), 1.86–2.07 (4H, m). MS m/e (M+H)$^+$=417, (M+NH$_4$)$^+$=434. Analysis calc'd for C$_{22}$H$_{28}$N$_2$O$_4$S: C, 63.44; H, 6.78; N, 6.73. Found: C, 63.15; H, 6.55; N, 6.49.

EXAMPLE 10

Preparation of
4-{3-[4-((N',N'-dimethylaminocarbonyl)-N-methylamino)-phenylsulfonyl]4-methoxytetrahydropyran Following the procedure from example 9, 4-{3-[4-((N',N'-dimethylaminocarbonyl)-N-methylamino)-phenysulfinyl]phenyl}-4-methoxytetrahydropyran (53 mg, 0.127 mmol) was converted to the title compound. Chromatography and recrystallization as previously described provided the pure title compound (47 mg, 86%) as a colorless solid. mp=109°–110° C.: $^1$H NMR (300 MHz, CDCl$_3$) δ7.97 (1H; br s), 7.80–7.88 (2H; m), 7.60 (1H; br d; J=8 Hz), 7.52 (1H; br d; J=8 Hz), 7.04 (2H; d; J=9.5 Hz), 3.80–3.91 (4H, m), 3.22 (3H, s), 2.95 (3H, s), 2.81 (6H, s), 1.86–2.07 (4H, m). MS m/e (M+H)$^+$=433, (M+NH$_4$)$^+$=450. Analysis calc'd for C$_{22}$H$_{28}$N$_2$O$_5$S(0.25 H$_2$): C, 60.46; H, 6.57; N, 6.41. Found: C, 60.44; H, 6.45; N, 6.32.

EXAMPLE 11

Preparation of
4-{3-[4-((N',N'-dimethylaminocarbonyl)aminomethyl)-benzyloxy]-5-fluorophenyl}-4-methoxytetrahydropyran Step 1, Preparation of 3-{[3-(4-bromomethyl)benzyloxy]-5-fluorophenyl}-4-methoxytetrahydropyran.

The desired compound was prepared according to the method of Example 1, step 5, except substituting α,α'-dibromo-p-xylene for 4-[(N',N'-dimethylaminocarbonyl)N-methylamino]benzyl chloride.

Step 2. Preparation of 4-{3-[4-((N',N'-dimethylaminocarbonyl)aminomethyl)benzyloxy]-5-fluorophenyl}-4-methoxytetrahydropyran.

To a solution of 1,1-dimethylurea (19 mg, 0.22 mmol), in DMF (1.0 mL), was added NaH (60% oil dispersion, 8.8 mg, 0.22 mmol). The reaction mixture was warmed to 50° C. and stirred for 0.5 hours. The reaction mixture was cooled to ambient temperature and a solution in DMF (1.0 mL), of 4-{3-[4-(bromomethyl)benzyloxy]-5-fluoro-phenyl}-4-methoxytetrahydropyran (90 mg, 0.22 mmol), prepared as in step 1, was added. The reaction mixture was stirred for four hours at ambient temperature, then H$_2$O (10 mL), and 1:1 ethyl acetate, pentane were added. The organic phase was washed with brine, dried over MgSO$_4$, filtered, and concentrated in vacuo. 4-{3-[(4-(N',N'-dimethylaminocarbonyl)aminomethyl)-benzyloxy]-5-fluorophenyl}-4-methoxytetrahydropyran (19 mg) was obtained by chromatography on silica gel (5% MeOH/CH$_2$Cl$_2$). $^1$H NMR (300 MHz, CDCl$_3$) δ7.30–7.45 (4H, m), 6.80 (1H, t, J=1.5 Hz), 6.71 (1H, dt, J=10.5, 2.2, 2.2 Hz), 6.6 (1H, dt, J=10.5, 2.2, 2.2 Hz), 5.03 (2H, s), 4.65 (1H, br s), 4.45 (2H, d, J=6 Hz), 3.79 to 3.85 (4H, m), 3.98 (3H, s), 3.93 (6H, s), 3.86 to 2.2 (4H, m). MS m/e 417 (M+H)$^+$, 434 (M+NH$_4$)$^+$.

EXAMPLE 12

Preparation of
4-{3-[4-((N',N'-dimethylaminocarbonyl)aminomethyl)-benzyloxy]phenyl}-4-methoxytetrahydropyran The desired compound is prepared according to the method of Example 11, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 13

Preparation of
4-{3-[4-((N',N'-dimethylaminocarbonyl)aminomethyl)-benzylthio]-5-fluorophenyl}-4-methoxytetrahydropyran The desired compound is prepared according to the method of Example 11, except substituting 4-(5-fluoro-3-thiophenyl)-4-methoxytetrahydrofuran, prepared as described in EPA 495 594, for 4-methoxy-4-(5-fluorophenoxy-3-yl)tetrahydropyran.

EXAMPLE 14

Preparation of
4-{3-[4-((N',N'-dimethylaminocarbonyl)aminomethyl)-benzylthio]phenyl}-4-methoxytetrahydropyran The desired compound is prepared according to the method of Example 12, except substituting 4-(3-thiophenyl)-4-methoxytetrahydrofuran, prepared as described in EPA 495 594, for 4-(5-fluoro-3-thiophenyl)-4-methoxytetrahydrofuran.

EXAMPLE 15

Preparation of
4-{3-[4-((N',N'-dimethylaminocarbonyl)aminomethylbenzyl)amino]phenyl}-4-methoxytetrahydropyran The desired compound is prepared according to the method of Example 11, except substituting 4-(3-aminophenyl)-4-methoxytetrahydropyran, prepared as in Example 4, for 4-methoxy-4-(5-fluoro-phenoxy-3-yl)tetrahydropyran.

EXAMPLE 16

Preparation of
4-{3-[4-(((N',N'-dimethylaminocarbonyl)-N-methylamino)methyl)benzyloxy]-5-fluorophenyl}-4-methoxytetrahydropyran The desired compound is prepared according to the method of Example 1, step 2, except substituting 4-{3-[4-((N',N'-dimethylaminocarbonyl)aminomethyl)benzyloxy]-5-fluoro-phenyl}-4-methoxytetrahydropyran, prepared as in Example 11, for 4-[(N', N'-dimethylaminocarbonyl)amino]benzoate.

EXAMPLE 17

Preparation of
4-{3-[4-(imidazolidin-2-on-1-ylmethyl)benzyloxy]-5-fluorophenyl}-4-methoxytetrahydropyran The desired compound was prepared according to the method of Example 11, step 2, except substituting 2-imidazolidinone for 1,1-dimethylurea. $^1$H NMR (300 MHz, CDCl$_3$) δ7.41(2H, d, J=9 Hz ),7.32 (2H, d, J=9 Hz), 6.81 (1H, t, J=1.5 Hz), 6.71 (1H, dq, J=10.5, 1.5, 1.5 Hz), 6.61 (1H, dt, J=10.5, 3, 3 Hz), 5.04 (2H, s), 4.39 (2H, s), 4.35 (1H, br s), 3.71 to 3.86 (4H, m), 3.28–3.35 (4H, m), 2.98 (3H, s), 1.85 to 2.05 (4H, m). MS m/e 415 (M+H)$^+$, 432 (M+NH$_4$)$^+$.

EXAMPLE 18

Preparation of
4-{3-[4-(imidazolidin-2-on-1-ylmethyl)benzyloxy]-phenyl}-4-methoxytetrahydropyran.

The desired compound is prepared according to the method of Example 17, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 19

Preparation of 4-{3-[4-(imidazolidin-2-on-1-ylmethyl)benzylthio]-5-fluorophenyl}-4-methoxytetrahydropyran The desired compound is prepared according to the method of Example 17, except substituting 4-(5-fluoro-3-thiophenyl)-4-methoxytetrahydrofuran, prepared as described in EPA 495 594, for 4-methoxy-4-(5-fluorophenoxy-3-yl)tetrahydropyran.

EXAMPLE 20

Preparation of 4-3-[4-(imidazolidin-2-on-1-ylmethyl)benzylthio]-phenyl}-4-methoxytetrahydropyran The desired compound is prepared according to the method of Example 19, except substituting 4-(3-thiophenyl)-4-methoxytetrahydrofuran, prepared as described in EPA 495 594, for 4-(5-fluoro-3-thiophenyl)-4-methoxytetrahydrofuran.

EXAMPLE 21

Preparation of 4-}3-[3-((N',N'-dimethylaminocarbonyl)-N-methylamino)benzyloxy]-5-fluorophenyl}-4-methoxytetrahydropyran Step 1. Preparation of 3-(O-t-butyldimethylsilyloxymethyl)aniline.

To a solution of 3-aminobenzyl alcohol (2.00 g, 16.2 mmol) and tert-butyldimethylsilyl chloride (2.90 g, 19.4 mmol) in CH$_2$Cl$_2$ (32.5 mL) was added triethylamine (7.45 mL, 53.5 mmol). The reaction mixture was stirred for 18 hours at ambient temperature and was then partitioned between ethyl acetate and H$_2$O. The organic phase was washed twice with H$_2$O, twice with brine, dried over MgSO$_4$, filtered, and concentrated in vacuo. 3-(O-t-butyldimethylsilyloxymethyl)aniline (2.18 g, 57%) was obtained as a yellow oil by chromatography on silica gel (30% ethyl acetate/hexane). $^1$H NMR (300 MHz, CDCl$_3$) δ7.10 (1H, t, J=7.5 Hz), 6.67–6.72 (2H, m), 6.56 (1H, br d, J=7.5 Hz), 4.66 (2H, s), 3.63 (2H, br s), 0.94 (9H, s), 0.09 (6H, s). MS m/e 238(M+H)$^+$, 255 (M+NH$_4$)$^+$.

Step 2. Preparation of O-t-butyldimethylsilyl-3-[(N'-methylaminocarbonyl)amino]benzyl alcohol.

To a solution under N$_2$ of 3-(O-t-butyldimethylsilyloxymethyl)aniline (900 mg, 3.79 mmol) in toluene (7.6 mL) was added methylisocyanate (0.45 mL, 7.58 mmol). The reaction mixture was stirred at 100° C. for 1.5 hours and was then cooled to ambient temperature and partitioned between ethyl acetate and H$_2$O. The organic phase was washed once with H$_2$O, twice with brine, dried over MgSO$_4$, filtered, and concentrated in vacuo. The oily residue crystallized on standing. The crystalline solid was washed twice with hexane to provide O-t-butyldimethylsilyl-3-[(N'-methylaminocarbonyl)amino]benzyl alcohol (641 mg, 57%). mp 110°–113° C. $^1$H NMR (300 MHz, CDCl$_3$) δ7.23–7.28 (2H, m), 7.17 (1H, d, J=7.5 Hz), 7.03 (1H, d, J=7.5 Hz), 6.68 (1H, br s), 5.0 (1H, br q, J=4 Hz), 4.69 (2H, s), 2.8 (3H, d, J=5 Hz), 0.93 (9H, s), 0.09 (6H, s). MS m/e 295(M+H)$^+$, 312 (M+NH$_4$)$^+$.

Step 3. Preparation of O-t-butyldimethylsilyl-3-[(N'-N'-dimethylaminocarbonyl)-N-methylamino]benzyl alcohol.

The desired compound was prepared according to the method of Example 1, step 2, except substituting O-t-butyldimethylsilyl-3-[(N'-methylaminocarbonyl)amino]benzyl alcohol, prepared as in step 2, for methyl 4-(N-methylaminocarbonyl)aminobenzoate. $^1$H NMR (300 MHz, CDCl$_3$) δ7.27 (1H, t, J=7.5 Hz), 7.00–7.06 (2H, m), 6.92 (1H, br d, J=7.5 Hz), 4.71 (2H, s), 3.21 (3H, s), 2.68 (6H, s),0.93 (9H, s) 0.09 (6H, s); MS m/e 323 (M+H)$^+$; 340 (M+NH$_4$)$^+$.

Step 4. Preparation of 3-[(N'-N'-dimethylaminocarbonyl)-N-methylamino]benzyl bromide.

To a solution of O-t-butyldimethylsilyl-3-[(N'-N'-methylaminocarbonyl)-N-methylamino]benzyl alcohol (371 mg, 1.15 mmol) in CH$_2$Cl$_2$ (5.7 mL) was added a solution of dibromotriphenylphosphorane (1.45 g, 3.45 mmol) in CH$_2$Cl$_2$ (5.7 mL). The reaction mixture was stirred for stirred for 1.5 hours at ambient temperature and was then partitioned between ethyl acetate and H$_2$O. The organic phase was washed twice with H$_2$O, twice with brine, dried over MgSO$_4$, filtered, and concentrated in vacuo. Pure 3-[(N'-N'-methylaminocarbonyl)-N-methylamino]benzyl bromide (282 mg, 90%) was obtained by chromatography on silica gel. $^1$H NMR (300 MHz, CDCl$_3$) δ7.29 (1H, t, J=7.5 Hz), 7.06–7.12 (2H, m), 6.98 (1H, br d, J=7.5 Hz), 4.46 (2H, s), 3.21 (3H, s), 2.72 (6H, s),0.93 (9H, s), 0.09 (6H, s). MS m/e 271/273 (M+H)$^+$, 288/290 (M+NH$_4$)$^+$.

Step 5. Preparation of 4-}3-[3-((N', N'-dimethylaminocarbonyl)-N-methylamino)benzyloxy]-5-fluorophenyl}-4-methoxytetrahydropyran.

The desired compound was prepared according to the method of Example 1, step 5, except substituting 3-[(N'-N'-methylaminocarbonyl)-N-methylamino]benzyl bromide, prepared as in step 4, for 4-[(N',N'-dimethylaminocarbonyl)-N-methylamino]benzyl chloride. $^1$H NMR (300 MHz, CDCl$_3$) δ7.34 (1H, t, J=7.5 Hz), 7.10–7.16 (2H, m), 7.02 (1H, br s, J=7.5 Hz), 6.81 (1H, br s), 6.72 (1H, br dr, J=9.9, 1.5, 1.5 Hz), 6.58 (1H, dt, J=9.9, 1.5, 1.5 Hz), 5.03 (2H, s), 3.80–3.86 (4H, m), 3.23 (3H, s), 2.98 (3H, s),2.68 (6H, s), 1.84–2.04 (4H, m). MS m/e 417 (M+H)$^+$; 434 (M+NH$_4$)$^+$. Analysis calc'd for C$_{23}$H$_{29}$FN$_2$O$_4$F: C, 66.33; H, 7.02; N, 6.73. Found C, 66.47; H, 7.01; N, 6.96.

EXAMPLE 22

Preparation of 4-{3-[3-((N',N'-dimethylaminocarbonyl)-N-methylamino)benzyloxy]phenyl}-4-methoxytetrahydropyran The desired compound is prepared according to the method of Example 21, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 23

Preparation of 4-{3-[3-((N',N'-dimethylaminocarbonyl)-N-methylaminobenzyl)amino]phenyl}-4-methoxytetrahydropyran The desired compound is prepared according to the method of Example 4, except substituting 3-[(N'-N'-methylaminocarbonyl)-N-methylamino]benzyl bromide, prepared as in Example 21, step 4, for 4-[(N',N'- dimethylaminocarbonyl)-N-methylamino]benzyl chloride.

EXAMPLE 24

Preparation of 4-{3-[3-((N',N'-dimethylaminocarbonyl)-N-methylamino)benzylthio]phenyl}-4-methoxytetrahydropyran The desired compound is prepared according to the method of Example 21, except substituting 4-(3-thiophenyl)-4-methoxytetrahydrofuran, prepared as described in EPA 495 594, for 4-(5-fluoro-3-hydroxyphenyl)-4-methoxytetrahydropyran.

EXAMPLE 25

Preparation of 4-{3-[3-((N',N'-dimethylaminocarbonyl)-N-methylamino)benzylthio]-5-fluorophenyl}-4-methoxytetrahydropyran The desired compound is prepared according to the method of Example 21, except substituting 4-(5-fluoro-3-thiophenyl)-4-methoxytetrahydrofuran, prepared as described in EPA 495 594, for 4-(5-fluoro-3-hydroxyphenyl)-4-methoxytetrahydropyran.

EXAMPLE 26

Preparation of 4-{3-[4-((N',N'-dimethylaminocarbonyl)-N-methylamino)phenylthio]-5-fluorophenyl}-4-methoxytetrahydropyran Step 1. Preparation of N-((N'-methylamino)carbonyl)-4-iodoaniline.

A solution of p-iodoaniline (5.0 g, 22.8 mmol) and methylisocyanate (2.7 mL, 45.6 mmol) in toluene (91 mL) was slowly warmed to 100° C. and stirred at that temperature for 1.5 h. The resulting thick slurry was cooled and filtered. The filter cake was washed with hexanes and dired under vacuum to provide the title compound as a beige solid (5.65 g, 90%). mp 230° C.: $^1$H NMR (300 MHz, CDCl$_3$) δ7.60 (2H; d; J=9 Hz), 7.10 (2H; d; J=9 Hz), 6.13 (1H, br s), 4.53 (1H; br s), 2.84 (3H; d; J=5 Hz). MS m/e (M+H)$^+$=277, (M+NH$_4$)$^+$=294.

Step 2. Preparation of N-(N',N'- dimethylaminocarbonyl)-N-methyl-4-iodoaniline.

Following the procedure described in example 8, step 4, but employing N-((N'-methyl amino)carbonyl)-4-iodoaniline in lieu of 3-[4-((N', N'-dimethylaminocarbonyl)amino)phenylthio]bromobenzene provided the the title compound as a colorless solid. mp 67°–68.5° C.: $^1$H NMR (300 MHz, CDCl$_3$) d 7.62 (2H; d; J=9 Hz), 6.82 (2H; d; J=9 Hz), 6.13 (1H, br s), 3.19 (3H, s), 2.72 (3H; s). MS m/e (M+H)$^+$=305, (M+NH$_4$)$^+$=322.

Step 3. Preparation of 4-{3-[4-((N',N'-dimethylaminocarbonyl)-N-methylamino)phenylthio]-5-fluorophenyl}-4-methoxytetrahydropyran.

The title compound was prepared according to the method of example 8, step 2, employing N-((N',N'-dimethylamino)carbonyl-N-methyl-4-iodoaniline in lieu of N-t-Boc-4-iodoaniline and 4-(5-fluoro-3-thiophenyl)-4-methoxytetrahydropyran (prepared according to the method in EP 420511) in lieu of 3-bromothiophenol. $^1$H NMR (300 MHz, CDCl$_3$) 67 7.41 (2H, d; J=9 Hz), 7.03–7.07 (3H, m), 6.90 (1H; ddd; J=10,2,1.5 Hz), 6.73 (1H; ddd; J=9,2,1.5 Hz),3.77–3.84 (4H, m), 3.25 (3H, s), 2.97 (3H, s), 2.75 (6H, s), 1.83–2.00 (4H, m). MS m/e 401 (M+H)$^+$=419, (M+NH$_4$)$^+$=436. Analysis calc'd for C$_{22}$H$_{27}$FN$_2$O$_3$S: C, 63.14; H, 6.50; N, 6.69. Found: C, 62.98; H, 6.36; N, 6.45.

EXAMPLE 27

Preparation of 4-{3-[2-((N',N'-dimethylaminocarbonyl)-N-methylamino)pyrid-5-ylthio]-5-fluorophenyl}-4-methoxytetrahydropyran Step 1. Preparation of N-((N',N'-dimethylaminocarbonyl)-N-methyl-2-amino)-5-bromopyridine.

Following the procedures described in Example 26, steps 1 and 2, 2-amino-5-bromopyridine was converted to the title compound as an oil. $^1$H NMR (300 MHz, CDCl$_3$) δ8.43 (1H; d; J=3 Hz), 7.63 (1H; dd; J=9,3 Hz), 6.79 (1H; dd; J=9,1 Hz), 3.28 (3H, s), 2.89 (6H, s),. MS m/e (M+H)$^+$=258/260.

Step 2. Preparation of 4-{3-[6-((N',N'-dimethylaminocarbonyl)-N-methylamino)pyrid-3-ylthio]-5-fluorophenyl}-4-methoxytetrahydropyran.

The title compound was prepared according to the method of example Example 26, step 3, employing N-((N',N'-dimethylaminocarbonyl)-N-methyl-2-amino)-5-bromopyridine in lieu of N-((N',N'-dimethylamino)carbonyl)-N-methyl-4-iodoaniline. $^1$H NMR (300 MHz, CDCl$_3$) δ8.4 (1H; d; J=3 Hz), 7.64 (1H; dd; J=9,3 Hz), 7.03 (1H; br s), 6.87–6.93 (2H; m), 6.68 (1H; dt; J=9,2,2 Hz), 3.78–3.86 (4H, m), 3.33 (3H, s), 2.97 (3H, s), 2.95 (6H, s), 1.83–2.00 (4H, m). MS m/e 401 (M+H)$^+$=420. Analysis calc'd for C$_{21}$H$_{26}$FN$_3$O$_3$S: C, 60.12; H, 6.25; N, 10.02. Found: C, 59.99; H,6.33; N, 9.89.

EXAMPLE 28

Preparation of 4-{3-[4-((N''-methylaminocarbonyl)-N-methylamino)phenylthio]phenyl}-4-methoxytetrahydropyran Step 1. Preparation of 3-(4-nitrophenylthio)bromobenzene.

A 1 liter flask was charged with a stir bar, THF (275mL), and sodium hydride (8.88 g, 0.22 mmol) and maintained under a nitrogen atmosphere. To this solution was added t-butanol (11.6 mL, 0.16 mmol) in a single portion. When gas evolution ceased, THF (300 mL) was added and then 3-bromobenzenethiol (35 g, 0.185 mmol) in 5 gm portions via syringe. After the exotherm ceased 4-bromonitrobenzene was added neat. The reaction was stirred for 1 h and became a thick slurry. The reaction was quenched by adding excess saturated ammonium chloride and partitioned between water and ether. The aqeous layer was adjusted to pH>12 with 15% aqueous sodium hydroxide and extracted with ether (3×). The combined organic layers were washed (1×, saturated ammonium chloride; 2×, brine), dried (MgSO$_4$), filtered, and concentrated under vacuum. Recrystallization from ether:hexanes provided the product as a yellow solid (31.86 g, 67%). The mother liqours were chromatographed over silica gel (1.25% ethyl acetate:hexanes) to provide 28.09 g of additional product which was slightly contaminated. Recrystalliztion as before provided after collecting two crops an additionsl 13.22 g of product (28%). $^1$H NMR (300 MHz, CDCl$_3$) δ8.11 (2H; d; J=9.5 Hz), 7.68 (1H; t; J=2 Hz), 7.57 (1H; br d; J=7.5 Hz), 7.46 (1H; d; J=7.5 Hz), 7.33 (1H; t; J=7.5 Hz), 7.24 (2H; d; J=9.5 Hz). MS m/e (M+H)$^+$=309/311, (M+NH$_4$)$^+$=327/329.

Step 2. Preparation of 3-(4-aminophenylthio)bromobenzene.

Following a modification of the procedure of He, Y.; et. al. (Synth. Commun. 1989, 19(17), 3047) 3-(4-nitrobenzenenethiol)bromobenzene (35.16 g, 0.113 mmol) was reduced, while stirring with a mechanical stirrer, with CuBH$_4$ (formed in situ by adding KBH$_4$ [17.9 g, 0.331 mmol] over 10 min. to a solution of substrate and Cu(I)Cl [14.0 g, 0.141 mmol] in methanol (850 mL)) while maintaining the internal reaction temperature between 5°-20° C. The excess reducing agent was quenched with water (500 mL) while maintaining the internal temperature below 20° C. with external cooling. The quenched reaction mixture was treated with 200 mL of 10% HCL and filtered through a celite plug to remove the spent reducing agent. The resulting solution was partitioned between ether and water. The aqueous phase was drawn off and extracted with ether (3×). The combined organic layers were washed (1×, saturated ammonium chloride; 2×, brine), dried (MgSO$_4$), filtered, and concentrated under vacuum to provide the title compound as a red solid (30.74 g, 95%). The product was of sufficient purity to carry on without further purification although 5-12% of the debrominated analog was typically isolated as an inseparable side-product. $^1$H NMR (300 MHz, CDCl$_3$) δ7.32 (2H; d; J=9.5 Hz), 7.24-6.98 (4H; m), 6.69 (2H; d; J=9.5 Hz), 3.83 (2H; br s). MS m/e (M+H)$^+$=280/282, (M+NH$_4$)$^+$=297/299.

Step 3. Preparation of N-acetyl-3-(4-aminophenylthio)-bromobenzene.

A 500 mL flask was charged with 3-(4-aminophenylthio)bromobenzene (21.53 g, 0.077 mmol), dry THF (290 mL), and pyridine (12.5 mL, 0.15 mmol). To the resulting solution was added neat acetyl chloride (6.04 mL, 0.85mL) over 10 min. After the exotherm was complete the reaction was judged to be complete by tlc. The reaction was quenched by adding an excess of saturated ammonium chloride. The two-phased mixture was partitoned between water and ether. The aqueous phase was drawn off and extracted with ether (3×). The combined organic layers were washed (1×, 10% aqueous HCl;2×, saturated aqueous sodium bicarbonate; 2×, brine), dried (MgSO$_4$), filtered, and concentrated under vacuum to provide the title compound as an orange solid (25.4 g, 99% ) which was carried on withour further purification. $^1$H NMR (300 MHz, CDCl$_3$) δ7.53 (2H; br d; J=9.5 Hz), 7.40 (2H; d; J=9.5 Hz), 7.11-7.38 (4H; m), 2.21 and 2.19 (3H; 2s). MS m/e (M+H)$^+$=322/324, (M+NH$_4$)$^+$=339/341.

Step 4. Preparation of 3-(4-aminophenylthio)-N-methyl-bromobenzene.

A THF (290 mL) solution of N-acetyl-3-(4-aminophenylthio)bromobenzene (34.55 g, 0.107 mmol) was cannulated slowly into a flask charged with dry THF (250 mL) and sodium hydride (5.14 g, 0.128 mmol). When gas evolution was complete, dry DMF (450 mL) and methyl iodide (13.3 mL, 0.214 mmol; filtered through a neutral alumina pad before addition to the reaction) were added sequentially. Reaction was judged to be complete after stirring at ambient temperature for 1 h and was quenched by carefully adding excess saturated ammonium chloride. The quenched mixture was partitioned between water and ether. The aqueous phase was drawn off and extracted with ether (3×). The combined organic layers were washed (2×, brine), dried (MgSO$_4$), filtered, and concentrated under high vacuum (to remove excess DMF) to provide the corresponding N-methyl-N-acetyl analog as a brown oil (39.9 g, 111%) which was carded on withour further purification. $^1$H NMR (300 MHz, CDCl$_3$) δ7.51 (1H; t; J=1.5 Hz), 7.07-7.47 (5H; m), 3.27 and 3.24 (3H; 2s), 1.89 3H; br s). MS m/e (M+H)$^+$=MS m/e (M+H)$^+$=339/341, (M+NH$_4$)$^+$=356/358. The N-methyl-N-acetyl analog was dissolved in ethanol (430 mL), 15% aqueous, sodium hydroxide was added (215 mL), and the resulting mixture was heated at reflux for 2.5 h at which point the reaction was complete. The reaction was cooled and partitioned between brine and ether. The aqueous phase was drawn off and extracted with ether (3×). The combined organic layers were washed (2×, saturated aqueous ammonium chloride; 2×, saturated aqueous sodium bicarbonate; 2×, brine), dried (MgSO$_4$), filtered, and concentrated under vacuum to provide the title compound as a brown oil (32.5 g, 104%) which was carried on withour further purification. $^1$H NMR (300 MHz, CDCl$_3$) δ7.34 (2H; br d; J=9.5 Hz), 7.17-7.20 (2H; m), 6.97-7.13 (2H; m), 6.60 (2H; br d; J=9.5 Hz), 2.86 (3H; 2s). MS m/e (M+H)$^+$=294/296, (M+NH$_4$)$^+$=311/313.

Step 5. Preparation of N-allyl-3-(4-aminophenylthio)-N-methyl-bromobenzene.

A fask was charged with dry DMSO (400 mL) and sodium hydride (4.93 g, 0.123 mmol) and maintained under a flow of nitrogen. To this suspension was added slowly 3-(4-aminophenylthio)-N-methyl-bromobenzene (30.13 g, 0.103 mmol) in dry DMSO via cannula. After gas evolution ceased, allyl bromide (22.3 mL, 0.257 mmol; passed through a neutral alumina plug prior to addition) was added in a single portion and the reaction was heated to 80° C. and maintained at that temperature under a nitrogen atmosphere. Alter 2 h the reaction was cooled, quenched carefully with saturated ammonium chloride, and partitioned between water and ether. The aqueous phase was drawn off and extracted with ether (4×). The combined organic layers were washed (5×, brine), dried (MgSO$_4$), filtered, and concentrated under vacuum to provide the title compound as a brown oil (33.9 g, 99%) which was purified by chromatography over silica gel (800 g silica gel; 1.25% ethyl acetate hexanes) to provide the title compound (25.34 g, 74%) as a thick light yellow oil. $^1$H NMR (300 MHz, CDCl$_3$) δ7.36 (2H; br d; J=9.5 Hz), 7.17-7.20 (2H; m), 6.96-7.13 (2H; m), 6.70 (2H; br d; J=9.5 Hz), 5.83 (1H; m), 5.18 (1H; dq; J=9.5, 1.5,1.5,1.4), 5.16 (1H; dq; J=9.5, 1.5,1.5,1.4), 3.97 (2H; dt; J=5,1.5,1.5), 2.99 (3H; 2s). MS m/e (M+H)$^+$=334/336.

Step 6. Preparation of 4-{3-[4-(N-allyl-N-methylamino)phenylthio]phenyl}-4-hydroxytetrahydropyran.

The title compound was prepared as described in example 4, step 2, except that 1.05 eqiuv of n-BuLi was employed in lieu of 2.5 eqiuv of n-BuLi and N-allyl-3-(4-aminophenylthio)-N-methyl-bromobenzene (4.07 g, 12.2 mmol) was employed in lieu of N-t-Boc-3 bromoaniline. Purification by chromatography over silica gel (20% ethyl acetate/hexanes) provided the pure title compound (3.51 g, 81%) as a thick oil. $^1$H NMR (300 MHz, CDCl$_3$) δ7.37 (2H; br d; J=9.5 Hz), 7.30 (1H; br s), 7.20 (2H; br d; J=6 Hz), ca. 6.96 (1H; m), 6.70 (2H; br d; J=9.5 Hz), 5.83 (1H; m), 5.18 (1H; dq; J=9.5, 1.5,1.5,1.4), 5.16 (1H; dq; J=9.5, 1.5,1.5,1.4), 3.97 (2H; dt; J=5, 1.5,1.5), 3.73-3.92 (4H; m), 2.99 (3H; 2s), 2.11 (2H; d,d,d; J=13,12,6 Hz), 1.63 (br d; J=13 Hz). MS m/e (M+H)$^+$=356.

Step 7. Preparation of 4-{3-[4-(N-allyl-N-methylamino)phenylthio]phenyl}-4-methoxytetrahydropyran Methylation was carried out as described in Example 4, step 4, except that the deprotonation with sodium hydride was carried out in dry THF (0.5M), 4-{3-[4-(N-allyl-N-methylamino)phenylthio]phenyl}-4-hydroxytetrahydropyran (3.51 g, 9.87 mmol) was employed in lieu of 4-(3-aminophenyl)-4-hydroxytetrahydropyran, and DMF (0.5M) was added after the methyl iodide was added. The product was purified by chromatography over silica gel (15% ethyl acetate/hexanes) to provide the pure title compound as a colorless oil (3.15 g, 86%). $^1$H NMR (300 MHz, CDCl$_3$) δ7.38 (2H; br d; J=9.5 Hz), 7.17–7.23 (2H; m), 7.11 (1H; dt; J=7.5, 1.5,1.5 Hz), 6.97 (1H; dt; J=7.5, 1.5,1.5 Hz), 6.70 (2H; d; J=9.5 Hz), 5.83 (1H; m), 5.18 (1H; dq; J=9.5, 1.5,1.5,1.4), 5.16 (1H; dq; J=9.5, 1.5,1.5,1.4), 3.96 (2H; dt; J=5, 1.5,1.5), 3.67–3.88 (4H; m), 2.99 (3H; 2s), 2.94 (3H; 2s), 1.74–2.03 (4H; m). MS m/e (M+H)$^+$=370.

Step 8. Preparation of 4-{3-[4-(N-methylamino)phenylthio]phenyl}-4-methoxytetrahydropyran.

An ethanol (25 mL) and water (12.5 mL) solution of 4-{3-[4-(N-allyl-N-methylamino)phenylthio]phenyl}-4-methoxytetrahydropyran (2.97 g, 7.49 mmol) was treated with tris(triphenylphosphine)ruthenium(II) chloride and heated at reflux for 2.5 h. The reaction was cooled to 0° C., ½ mL of glacial acetic added, the resulting mixture stirred at ambient temperature for 0.3 h, and filtered through a celite pad. The filter pad was washed with ethyl acetate and water. The combined filtrates were partitioned between ethyl acetae and water. The organic layer was washed (2X, saturated aqueous sodium bicarbonate; 2X, water; 1X, brine), dried (MgSO$_4$), filtered and concentrated under vacuum. Purification by chromatography over silica gel (15% ethyl acetae:hexanes) provided the pure title compound as a solid (2.09 g, 85%). mp 87°–88° C.: $^1$H NMR (300 MHz, CDCl$_3$) δ7.35 (2H; br d; J=9.5 Hz), 7.18–7.21 (2H; m), 7.11 (1H; dt; J=7.5, 1.5,1.5 Hz), 6.97 (1H; dt; J=7.5, 1.5,1.5 Hz), 6.62 (2H; d; J=9.5 Hz), 3.74–3.88 (4H; m), 2.96 (3H; 2s), 2.87 (3H; br s), 1.83–2.03 (4H; m). MS m/e (M+H)$^+$=330, (M+NH$_4$)$^+$=347.

Step 9. preparation of 4-{3-[4-((N'-methylaminocarbonyl)-N-methylamino)phenylthio]phenyl}-4-methoxytetrahydropyran.

The desired compound (246 mg, 84%) was prepared according to the method of Example 26, step 1, except substituting 4-{3-[4-(N-methylamino)phenylthio]phenyl}-4-methoxytetrahydropyran (250 mg, 0.76 mmol) for 4-iodoaniline. mp 150°–151° C.: $^1$H NMR (300 MHz, CDCl$_3$) δ7.48 (1H, m), 7.26–7.40 (5H, m), 7.16 (2H, d, J=9 Hz), ca. 4.28 (1H, br m), 3.80–3.91 (4H; m), 3.27 (3H, s), 2.98 (3H, s), 2.75 (3H; d; J=4H), 1.88–2.07 (4H, m). MS m/e (M+H)$^+$=387, (M+NH$_4$)$^+$=404; Analysis calc'd for C$_{21}$H$_{26}$N$_2$O$_3$S: C, 65.26; H, 6.78; N, 7.25. Found: C, 64.97; H, 6.81; N, 7.04.

EXAMPLE 29

Preparation of 4-{3-[4-((4-morpholinocarbonyl)-N-methylamino)-phenylthio]phenyl}-4-methoxytetrahydropyran A THF (2.7 mL) solution of 4-{3-[4-(N-methylamino)phenylthio]phenyl}-4-methoxytetrahydropyran (95 mg, 0.267 mmol; prepared in step 9 of Example 28 was cooled to −40° C. under a dry nitrogen atmosphere and treated with a THF solution of lithium hexamethyldisilazide (LHMDS; 0.32 mL of a 1M solution, 0.32 mmol). The resulting solution was stirred for 1 h at −40° C. and morpholinocarbamoyl chloride (47 μL, 0.40 mmol) was added neat via syringe. The cooling bath was removed and the reaction was stirred at ambient temperature for 1 h. The reaction was quenched by the addition of excess water. The resulting mixture was partitioned between ethyl acetate and saturated ammonium chloride. The layers were separated and the organic layer was washed (1X, sat'd ammonium chloride; 1X, water; 2X, brine), dried (MgSO$_4$), filtered and concentrated under vacuum. The resulting residue was chromatographed over silica gel (60% EtOAc:Hex) to give a light yellow oil. The oil was dissolved in ethyl acetate, treated with decolorizing carbon, and filtered through a Celite® pad. Removal of the volatiles under vacuum and drying the residue under high vacuum provided the title compound as a colorless oil (75 mg, 64%). $^1$H NMR (300 MHz, CDCl$_3$) δ7.48 (1H, m), 7.26–7.40 (5H, m), 7.16 (2H, d, J=9 Hz), ca. 4.28 (1H, br m), 3.80–3.91 (4H; m), 3.27 (3H, s), 2.98 (3H, s), 2.75 (3H; d; J=4 Hz), 1.88–2.07 (4H, m). MS m/e (M+H)$^+$=387, (M+NH$_4$)$^+$=404; Analysis calc'd for C$_{21}$H$_{26}$N$_2$O$_3$S: C, 65.26; H, 6.78; N, 7.25. Found: C, 64.97; H, 6.81; N, 7.04.

EXAMPLE 30

Preparation of 4-{3-[4-((4-morpholinocarbonyl)-N-methylamino)-phenylthiol-5-fluorophenyl}-4-methoxytetrahydropyran Step 1. Preparation of N-Boc-N-methyl-4-iodoaniline.

The desired compound is prepared as described in example 8, step 4, except employing N-Boc-4-iodoaniline (prepared from p-amino-iodoaniline as described in example 4, step 1, for the preparation of N-t-Boc-3-bromoaniline) in lieu of 3-[4-((N', N'-dimethylaminocarbonyl)amino) phenylthio]bromobenzene.

Step 2. Preparation of 4-{3-[4-((4-N-Boc-N-methylamino)phenylthio]-5-fluorophenyl}-4-methoxytetrahydropyran The title compound was prepared according to the method of Example 26, step 2, employing N-Boc-N-methyl-4-iodoaniline in lieu of N-((N',N'-dimethylamino)carbonyl)-N-methyl-4-iodoaniline.

Step 3. Preparation of 4-{3-[4-((4-N-methylamino)phenylthio]-5-fluorophenyl}-4-methoxytetrahydropyran The desired compound is prepared by exposure of 4-{3-[4-((4-N-t-Boc-N-methylamino)phenylthio]-5-fluorophenyl}-4-methoxytetrahydropyran to a 0.25M solution of 1:1 trifluroacetic acid:CH$_2$Cl$_2$ for 1 h at ambient temperature. The volatiles are removed under vacuum and the resulting salt is partitoned between ethyl acetate and excess 10% aqueous sodium hydroxide. The organic layer is drawn off, washed (2X, brine), dried (NaSO$_4$), filtered, and concentrated under vacuum. The resulting residue is of sufficient purity to carry on without further purification.

Step 4. Preparation of 4-{3-[4-((4-morpholinocarbonyl)-N-methylamino)phenylthio]-5-fluorophenyl}-4-methoxytetrahydropyran.

The title compound is prepared according to the method of Example 29, but employing 4-{3-[4-((4-methylamino)phenylthio]-5-fluorophenyl}-4-methoxytetrahydropyran in lieu of 4-{3-[4-((4-N-methylamino)phenylthio]-phenyl}-4-methoxytetrahydropyran.

EXAMPLE 31

Preparation of
4-{3-[4-(((4-methylpiperazinyl)carbonyl)-N-methylamino)phenylthio]phenyl}-4-methoxytetrahydropyran To a methylene chloride (16 mL) solution of 4-{3-[4-(N-methylamino)phenylthio]phenyl}-4-methoxytetrahydropyran (517 mg, 1.57 mmol; prepared in step 8 of Example 29) was added triethylamine (0.22 mL, 1.57 mmol) and triphosgene (23.3 mg, 0.79 mmol) in methylenechloride (5 mL). The resulting solution was stirred at ambient temperature for 0.5 h, N-methylpiperazine (0.70 mL, 6.3 mmol) was added, and the mixture was stirred for another hour at ambient temperature. The reaction mixture was partitioned between ethyl acetate and 10% aqueous HCl. The layers were separated and the organic layer was washed (1×, saturated sodium bicarbonate; 2×, water; 2×, brine), dried (MgSO$_4$), filtered and concentrated under vacuum. The resulting residue was chromatographed over silica gel (5% ethanol:methylene chloride+1% ammonium hydroxide) to give a light yellow oil. The oil was dissolved in ethyl acetate, treated with decolorizing carbon, and filtered through a celite pad. Removal of the volatiles under vacuum and drying the residue under high vacuum provided the title compound as a colorless oil (482 mg, 67%). 1H NMR (300 MHz, CDCl$_3$) $\delta$7.48 (1H, m), 7.15-7.38 (5H, m), 7.04 (2H, d, J=9 Hz), 3.77-3.89 (4H; m), 3.2-3.28 (4H; m), 3.24 (3H, s), 2.97 (3H, s), 2.20-2.28 (4H; m), 2.24 (3H; s), 1.88-2.04 (4H, m). MS m/e (M+H)$^+$=456; Analysis calc'd for C$_{25}$H$_{33}$N$_3$O$_3$S: C, 65.91; H, 7.30; N, 9.22. Found: C, 65.86; H, 7.25; N, 9.22.

EXAMPLE 32

Preparation of
4-{3-[4-(((4-methylpiperazinyl)carbonyl)-N-methylamino)-phenylthio]-5-fluorophenyl}-4-methoxytetrahydropyran The desired compound is prepared according to the procedure of Example 31 except 4-{3-[4-((4-N-methylamino)phenylthio]-5-fluorophenyl}-4-methoxytetrahydropyran is employed in lieu of 4-{3-[4-(N-methylamino)phenylthio]phenyl}-4-methoxytetrahydro pyran.

EXAMPLE 33

Preparation of
4-{3-[4-(((4-methylpiperazinyl)carbonyl)-N-methylamino)phenylthio]phenyl}-4-methoxytetrahydropyran hydrochloride salt A methylene chloride (3 mL) solution of 4-{3-[4-(((4-methylpiperazinyl)carbonyl)-N-methylamino)phenylthio]phenyl}-4-methoxytetrahydropyran (132 mg, 0.29 mmol) was treated with a 4M solution of HCl in dioxane (7.3 mL, 0.29 mmol) and stirred at ambient temperature for 1 h. Addition of ether (20 mL) precipitated a colorless solid which was collected by filtration. The filter cake was washed thoroughly with ether and dried under vacuum to provide the title compound as a colorless solid. mp 154°-155° C.: 1H NMR (300 MHz, DMSO-D$_6$) $\delta$7.14-7.42 (5H, m), 3.63-3.77 (4H; m), 2.70-3.40 (8H; m), 3.16 (3H, s), 2.86 (3H, s), 2.72 (3H; br s), 1.80-1.93 (4H, m). MS m/e (M−HCl+H)$^+$=456; Analysis calc'd for C$_{25}$H$_{33}$N$_3$O$_3$S(2HCl): C, 56.81; H, 6.67; N, 7.95. Found: C, 56.91; H, 6.67; N, 7.56.

EXAMPLE 34

Preparation of
4-{3-[4-(((4-methylpiperazinyl)carbonyl)-N-methylamino)phenylthio]-5-fluorophenyl}-4-methoxytetrahydropyran hydrochloride The desired compound is prepared according to the procedure of Example 33 except 4-{3-[4-((4-N-methylamino)phenylthio]-5-fluorophenyl}-4-methoxytetrahydropyran is employed in lieu of 4-{3-[4-(N-methylamino)phenylthio]phenyl}-4-methoxytetrahydro pyran.

EXAMPLE 35

Preparation of 4-{3-[4-(((N'-allyl-N'-methyl amino)carbonyl)-N-methylamino)phenyl-thio]phenyl}-4-methoxytetrahydropyran Step 1. Preparation of 4-{3-[4-(((N'-allyl-amino)carbonyl)-N-methylamino)phenylthio]phenyl}-4-methoxytetrahydropyran.

The title compound was prepared as in Example 31 except that allylamine was employed in lieu of N-methylpiperazine. The resulting residue was chromatographed over silica gel (45% ethyl acetate:hexanes) to provide the title compound as a colorless oil (332 mg, 97%) which was contaminated with an unidentified impurity which also contained an allyl group. 1H NMR (300 MHz, CDCl$_3$) $\delta$7.48 (1H, br s), 7.27-7.40 (5H, m), 7.18 (2H, d, J=9 Hz), 5.81 (1H; d,d,t; J=18,10.5,5.5,5.5 Hz), 5.07 (1H; d,q; J=18,1.5,1.5,1.5 Hz), 5.03 (1H; dq; J=10.5,1.5,1.5,1.5 Hz), 3.78-3.87 (6H; m), 3.27 (3H, s), 2.98 (3H, s), 1.88-2.04 (4H, m). MS m/e (M+H)$^+$=413, (M+NH$_4$)$^+$=430.

Step 2. Preparation of 4-{3-[4-(((N'-allyl-N'-methyl amino)carbonyl)-N-methylamino)phenylthio]phenyl}-4-methoxytetrahydropyran The title compound was prepared by N-methylation following the procedure described in Example 1, step 2, but employing 4-{3-[4-(((N'-allyl-amino)carbonyl)-N-methylamino)phenylthio]phenyl}-4-methoxytetrahydropyran (390 mg, 0.95 mmol) in lieu of methyl 4-(N-methylaminocarbonyl)amino-benzoate. Purification was achieved by chromatography over silica gel (35% ethyl acetae:hexanes) and by preparative tlc (50% ethyl acetate:hexanes) to provide the title compound as a colorless oil (94 mg, 23%). 1H NMR (300 MHz, CDCl$_3$) $\delta$7.16-7.38 (6H, m), 7.03 (2H, d, J=9 Hz), 5.66 (1H; d,d,t; J=16.5,11,6,6 Hz), 5.13 (1H; d,q; J=11,1.5,1.5,1.5 Hz), 5.08 (1H; dq; J=16.5,1.5,1.5,1.5 Hz) 2.59 (3H; s), 1.86-2.05 (4H; m). MS m/e (M+H)$^+$=427, (M+NH$_4$)$^+$=444. Analysis calc'd for C$_{24}$H$_{30}$N$_2$O$_3$S: C, 67.58; H, 7.09; N, 6.57. Found: C, 67.73; H, 7.33; N, 6.46.

EXAMPLE 36

Preparation of
4-{3-[4-(((4-methylpiperazinyl)carbonyl)-N-methylamino)phenylthio]-5-fluorophenyl}-4-methoxytetrahydropyran The desired compound is prepared according to the method described in Example 35 except 4-{3-[4-((4-N-methylamino)phenylthio]-5-fluorophenyl }-4-methoxytetrahydropyran is employed in lieu of 4-{3-[4-((4-N-methylamino)phenylthio]phenyl}-4-methoxytetrahydropyran.

EXAMPLE 37

Preparation of 4-{3-[4-((N",N"-dimethyl-N'-cyano-N-methylguanadinyl)phenylthio]phenyl}-4-methoxytetrahydropyran A reasealable tube was charged with N,N-dimethylamine hydrochloride (85 mg, 1.05 mmol), diphenyl cyanocarbonimidate (750 mg, 3.15 mmol), diisopropyethylamine (0.22 mL, 1.26 mmol), and dry THF (4.2 mL). The tube was sealed and stirred at ambient temperature for 4 h and at 50° C. for 3 days. The reaction was partitioned between ethyl acetate and saturated sodium bicarbonate. The organic layer was drawn off and washed (2×, water; 1×, brine), dried (MgSO4), filtered and concentrated under vacuum. Purification by chromatography over silica gel (10% ethyl acetate:- hexanes provided O-phenyl-N-cyano-N',N'-dimethylurea (203 mg, 100%). The desired title compound was prepared according to the method of Example 29, except substituting O-phenyl-N-cyano-N',N'-dimethylurea for morpholinocarbamoyl chloride. Purification by chromatography over silica gel (70% ethyl acetate) and recrystallization (ether:hexanes) of the resultant material provided the pure title compound as a colorless solid (102.5 mg, 53%). mp=114.5°-115° C. $^1$NMR (300 MHz, CDCl3) δ7.25-7.39 (5H, m), 7.18 (1H; dt; J=7.5, 1.5, 1.5 Hz), 6.98 (2H; d; J=9.5 Hz), 3.77-3.89 (4H, m), 3.43 (3H, s), 2.96 (3H, s), 2.87 (6H, s), 1.86-2.04 (4H, m). MS m/e (M+H)$^+$=425, (M+NH4)$^+$=442; Analysis calc'd for $C_{23}H_{28}N_4O_2S$: C, 65.07; H, 6.65; N, 13.20. Found: C, 64.83; H, 6.40; N, 12.92.

EXAMPLE 38

Preparation of 4-{3-[4-((N',N'-dimethylaminocarbonyl)-N-methylamino)-phenylsulfinyl]-5-fluorophenyl}-4-methoxytetrahydropyran Following the procedure from Example 9 except that 4-{3-[4-((N',N'-dimethylaminocarbonyl)-N-methylamino)-phenylthio]-5-fluorophenyl}-4-methoxytetrahydropyran was employed in lieu of 4-{3-[4-((N',N'-dimethylaminocarbonyl)-N-methylamino)-phenylthio]phenyl}-4methoxytetrahydropyran, provided the title compound. $^1$H NMR (300 MHz, CDCl3) δ7.59 (2H; d; J=9.5 Hz), 7.47 (1H; t; J=1.5 Hz), 7.25-7.27 (1H; m), 7.17 (1H; d,d,d; J=9,1.5,1 Hz), 7.09 (2H, d, J=9.5 Hz), 3.82-3.87 (4H; m), 3.22 (3H; s), 2.95 (3H, s), 2.75 (6H, s), 1.86-2.05 (4H, m). MS m/e (M+H)$^+$=435, (M+NH4)$^+$=452.

EXAMPLE 39

Preparation of 4-{3-[4-((N', N'-dimethylaminocarbonyl)-N-methylamino)phenylsulfonyl]-5-fluorophenyl}-4-methoxytetrahydropyran Following the procedure from Example 9 except that 4-{3-[4-((N',N'-dimethylaminocarbonyl)-N-methylamino)-phenylsulfinyl]-5-fluorophenyl}-4-methoxytetrahydropyran was employed in lieu of 4-{3-[4-((N',N'-dimethylaminocarbonyl)-N-methylamino)-phenylthio]phenyl}-4-methoxytetrahydropyran, to provide the title compound. Mp=134.5°-135.5° C.: $^1$H NMR (300 MHz, CDCl3) δ7.86 (2H; d; J=9 Hz), 7.74 (1H; t; J=1 Hz), 7.52 (1H; ddd; J=8,3,2 Hz), 7.27-7.33 (1H; m), 7.05 (2H; d; J=9 Hz), 3.80-3.87 (4H, m), 3.22 (3H, s), 2.97 (3H, s), 2.83 (6H, s), 1.86-2.05 (4H, m). MS m/e (M+H)$^+$=451, (M+NH4)$^+$=468.

The compounds represented in Table 2 are prepared by treatment of arylalkylamine 15 with trimethylsilylisocyanate, with R$^8$NCO, or with RLi and R$^7$R$^8$NCOCl as described in Scheme 2.

TABLE 2

| Example | R$^6$ | R$^7$ | R$^8$ |
|---|---|---|---|
| 40 | Me | H | H |
| 41 | Me | H | Me |
| 42 | Me | H | Et |
| 43 | Me | H | Pr |
| 44 | Me | H | Bu |
| 45 | Me | Et | Me |
| 46 | Me | Pr | Me |
| 47 | Me | Bu | Me |
| 48 | Me | Et | Et |
| 49 | Me | Pr | Pr |
| 50 | Me | Bu | Bu |
| 51 | Me | Ph | H |
| 52 | Me | Ph | Me |
| 53 | Me | piperidinyl | |
| 54 | Me | morpholinyl | |
| 55 | Me | thiomorpholinyl | |
| 56 | Me | N-methylpiperazinyl | |
| 57 | Me | piperazinyl | |
| 58 | Et | H | Me |
| 59 | Et | Me | Me |
| 60 | Pr | H | Me |
| 61 | Pr | Me | Me |
| 62 | Bu | H | Me |

TABLE 2-continued

| 63 | Bu | Me | Me |

The compounds represented in Table 3 are prepared by reaction of isocyanate 19 with HNR$^7$R$^8$ as described in Scheme 3.

TABLE 3

[Structure of isocyanate 19 reacting with R$^7$R$^8$NH to give urea product]

| Example | R$^7$ | R$^8$ |
|---|---|---|
| 64 | H | Me |
| 65 | H | Et |
| 65 | H | Pr |
| 66 | H | Bu |
| 67 | Me | Me |
| 68 | Me | Et |
| 69 | Me | Pr |
| 70 | Me | Bu |
| 71 | Et | Et |
| 72 | Pr | Pr |
| 73 | Bu | Bu |
| 74 | Ph | H |
| 75 | Ph | Me |
| 76 | | piperidinyl-N— |
| 77 | | morpholinyl-N— |
| 78 | | thiomorpholinyl-N— |
| 79 | | 4-methylpiperazinyl-N— |
| 80 | | piperazinyl-N— |

The compounds represented in Table 4 are prepared according to the method described in Schemes 4a and 4b.

TABLE 4

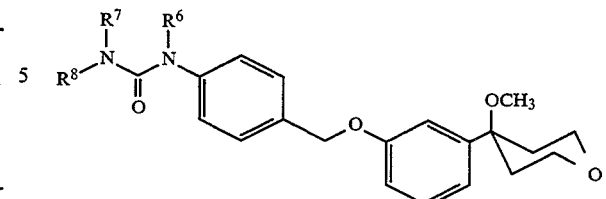

| Example | R$^6$ | R$^8$ | R$^7$ |
|---|---|---|---|
| 81 | H | —CH$_2$CH$_2$CH$_2$Br | H |
| 82 | H | —CH$_2$CH$_2$CH$_2$Br | Me |
| 83 | H | —CH$_2$CH$_2$CH$_2$NH$_2$ | H |
| 84 | H | —CH$_2$CH$_2$CH$_2$NH$_2$ | Me |
| 85 | H | —CH$_2$CH$_2$CH$_2$OH | H |
| 86 | H | —CH$_2$CH$_2$CH$_2$OH | Me |
| 87 | H | —CH$_2$CH$_2$CH$_2$COOH | H |
| 88 | H | —CH$_2$CH$_2$CH$_2$COOH | Me |
| 89 | H | —CH$_2$CH$_2$CH$_2$COOEt | H |
| 90 | H | —CH$_2$CH$_2$CH$_2$COOEt | Me |
| 91 | H | —CH$_2$CH$_2$CH$_2$CONHCH$_3$ | H |
| 92 | H | —CH$_2$CH$_2$CH$_2$CONHCH$_3$ | Me |
| 93 | Me | —CH$_2$CH$_2$CH$_2$Br | H |
| 94 | Me | —CH$_2$CH$_2$CH$_2$Br | Me |
| 95 | Me | —CH$_2$CH$_2$CH$_2$NH$_2$ | H |
| 96 | Me | —CH$_2$CH$_2$CH$_2$NH$_2$ | Me |
| 97 | Me | —CH$_2$CH$_2$CH$_2$OH | H |
| 98 | Me | —CH$_2$CH$_2$CH$_2$OH | Me |
| 99 | Me | —CH$_2$CH$_2$CH$_2$COOH | H |
| 100 | Me | —CH$_2$CH$_2$CH$_2$COOH | Me |
| 101 | Me | —CH$_2$CH$_2$CH$_2$COOEt | H |
| 102 | Me | —CH$_2$CH$_2$CH$_2$COOEt | Me |
| 103 | Me | —CH$_2$CH$_2$CH$_2$CONHCH$_3$ | H |
| 104 | Me | —CH$_2$CH$_2$CH$_2$CONHCH$_3$ | Me |

We claim:

1. A compound or pharmaceutically acceptable salt thereof selected from the group consisting of:

4-{3-[4-((N',N'-dimethylaminocarbonyl)-N-methylamino)phenylthio]-5-fluorophenyl}-4-methoxytetrahydropyran, 4-{3-[2-((N',N'-dimethylaminocarbonyl)-N-methylamino)pyrid-5-ylthio]-5-fluorophenyl}-4-methoxytetrahydropyran, 4-{3-[4-((N'-methylaminocarbonyl)-N-methylamino)-phenylthio]phenyl}-4-methoxytetrahydropyran, 4-{3-[4-((4-morpholinocarbonyl)-N-methylamino)-phenylthio]phenyl}-4-methoxytetrahydropyran, 4-{3-[4-((4-morpholinocarbonyl)-N-methylamino)-phenylthio]-5-fluorophenyl}-4-methoxytetrahydropyran, 4-{3-[4-(((4-methylpiperazinyl)carbonyl)-N-methylamino)phenylthio]phenyl}-4-methoxytetrahydropyran, 4-{3-[4-(((4-methylpiperazinyl)carbonyl)-N-methylamino)phenylthio]-5-fluorophenyl}-4-methoxytetrahydropyran, 4-{3-[4-(((4-methylpiperazinyl)carbonyl)-N-methylamino)phenylthio]phenyl}-4-methoxytetrahydropyran hydrochloride, 4-{3-[4-(((4-methylpiperazinyl)carbonyl)-N-methylamino)phenylthio]-5-fluorophenyl}-4-methoxytetrahydropyran hydrochloride, 4-{3-[4-((N'-allyl-N'-methylamino)carbonyl)-N-methylamino)phenylthio]phenyl}-4-methoxytetrahydropyran, 4-{3-[4-(((4-methylpiperazinyl)carbonyl)-N-methylamino)phenylthio]-5-fluorophenyl}-4-methoxytetrahydropyran, 4-{3-[4-(N'',N'''-dimethyl-N'-cyano-N-methyl-guanidinyl)phenylthio]phenyl}-4-methoxytetrahydropyran, 4-{-3-[4-((N',N'-dimethylaminocarbonyl)-N-methylamino)phenylsulfinyl]phenyl}-4-methoxytetrahydropyran, 4-{-3-[4-((N',N'-dimethylaminocarbonyl)-N-methylamino)phenylsulfonyl]phenyl}-4-methoxytetrahydropyran, 4-{-3-[4-((N',N'-dimethylaminocarbonyl)-N-methylamino)phenylsulfinyl]-5-fluorophenyl}-4-methoxytetrahydropyran, and 4-{-3-[4-((N',N'-dimethylaminocarbonyl)-N-methylamino)phenylsulfonyl]-5-fluorophenyl}-4-methoxytetrahydropyran.

2. A pharmaceutical composition comprising a therapeutically effective amount of a compound as defined by claim 1 in combination with a pharmaceutically acceptable carder.

3. A method of inhibiting 5-lipoxygenase enzyme activity in a mammal in need of such treatment comprising administering an effective amount of a compound as defined by claim 1.

* * * * *

UNITED STATES PATENT AND TRADEMARK OFFICE
CERTIFICATE OF CORRECTION

PATENT NO. : 5,432,194
DATED : July 11, 1995
INVENTOR(S) : Joseph F. Dellaria; Anwer Basha; Lawrence A. Black; Linda J. Chernesky; Wendy Lee;

It is certified that error appears in the above-indentified patent and that said Letters Patent is hereby corrected as shown below:

COLUMN 46, LINE 7: Delete "carder"
                     Insert --carrier--

Signed and Sealed this

Twelfth Day of December, 1995

Attest:

BRUCE LEHMAN

Attesting Officer

Commissioner of Patents and Trademarks